US011568991B1

(12) United States Patent
Jain et al.

(10) Patent No.: US 11,568,991 B1
(45) Date of Patent: Jan. 31, 2023

(54) MEDICAL DIAGNOSTIC TOOL WITH NEURAL MODEL TRAINED THROUGH MACHINE LEARNING FOR PREDICTING CORONARY DISEASE FROM ECG SIGNALS

(71) Applicant: Heart Input Output, Inc., Pittsburgh, PA (US)

(72) Inventors: Utkars Jain, Pittsburgh, PA (US); Adam A. Butchy, Pittsburgh, PA (US); Michael T. Leasure, Pottstown, PA (US)

(73) Assignee: HEART INPUT OUTPUT, INC., Pittsburgh, PA (US)

( * ) Notice: Subject to any disclaimer, the term of this patent is extended or adjusted under 35 U.S.C. 154(b) by 0 days.

(21) Appl. No.: 17/382,909

(22) Filed: Jul. 22, 2021

Related U.S. Application Data

(60) Provisional application No. 63/055,603, filed on Jul. 23, 2020.

(51) Int. Cl.
*G16H 50/20* (2018.01)
*G16H 40/63* (2018.01)
*G06N 3/04* (2006.01)
*G06N 3/08* (2006.01)

(52) U.S. Cl.
CPC ............... *G16H 50/20* (2018.01); *G06N 3/04* (2013.01); *G06N 3/088* (2013.01); *G16H 40/63* (2018.01)

(58) Field of Classification Search
CPC ............................ A61B 5/7257; A61B 5/1118
See application file for complete search history.

(56) References Cited

U.S. PATENT DOCUMENTS

| 8,364,248 B2 | 1/2013 | Zhang |
| 8,626,274 B2 | 1/2014 | Chiu et al. |
| 10,089,451 B2 | 10/2018 | Feng et al. |
| 10,262,111 B2 | 4/2019 | Dziubinski et al. |
| 2008/0103403 A1 | 5/2008 | Cohen |
| 2010/0217144 A1 | 8/2010 | Arenare |
| 2017/0086672 A1* | 3/2017 | Tran ....................... G16H 40/63 |
| 2018/0055397 A1 | 3/2018 | Salah et al. |
| 2019/0090774 A1 | 3/2019 | Yang et al. |
| 2019/0183431 A1 | 6/2019 | Attia et al. |
| 2019/0374166 A1 | 12/2019 | Charles et al. |
| 2020/0151516 A1* | 5/2020 | Anushiravani ......... G10L 15/16 |

(Continued)

FOREIGN PATENT DOCUMENTS

| WO | WO 2001/058350 A1 | 8/2001 |
| WO | WO 2019/038109 A1 | 2/2019 |

(Continued)

*Primary Examiner* — Fabricio R Murillo Garcia
(74) *Attorney, Agent, or Firm* — K&L Gatss LLP

(57) ABSTRACT

A diagnostic tool includes a sensor for capturing at least one biosignal produced by a patient's heart and a computer device that implements a neural network iteratively trained via machine learning to generate a prediction about a heart condition of the patient. After the neural network is trained, the computer device can convert the at least one biosignal to a multi-dimensional input matrix for the deep neural network generated from a number (N) of biosignals captured by the sensor. The computer device then processes the multi-dimensional input matrix through the deep neural network, which subsequently outputs the prediction about the heart condition of the patient.

22 Claims, 11 Drawing Sheets

(56) References Cited

U.S. PATENT DOCUMENTS

| | | |
|---|---|---|
| 2020/0196897 A1 | 6/2020 | Biswas et al. |
| 2020/0202527 A1* | 6/2020 | Choi ..................... G06V 40/18 |
| 2020/0205687 A1 | 7/2020 | Rubin et al. |
| 2020/0356817 A1* | 11/2020 | Walters ................ G06K 9/6267 |
| 2021/0038102 A1 | 2/2021 | Boleyn et al. |
| 2021/0100471 A1 | 4/2021 | Yu et al. |
| 2021/0106240 A1 | 4/2021 | Kerman et al. |
| 2021/0106241 A1* | 4/2021 | Kerman ............... A61B 5/7267 |
| 2021/0174961 A1 | 6/2021 | Dutt et al. |
| 2021/0204884 A1 | 7/2021 | Ravishankar et al. |
| 2021/0321890 A1* | 10/2021 | Iyer ..................... A61B 5/7221 |

FOREIGN PATENT DOCUMENTS

| | | |
|---|---|---|
| WO | WO 2019/100565 A1 | 5/2019 |
| WO | WO 2020/004369 A1 | 1/2020 |
| WO | WO 2021/031155 A1 | 2/2021 |

* cited by examiner

MEDICAL DIAGNOSTIC TOOL WITH NEURAL MODEL TRAINED THROUGH MACHINE LEARNING FOR PREDICTING CORONARY DISEASE FROM ECG SIGNALS

PRIORITY CLAIM

The present application claims priority to U.S. Provisional Patent Application No. 63/055,603, titled MEDICAL DIAGNOSTIC TOOL WITH NEURAL MODEL TRAINED THROUGH MACHINE LEARNING FOR PREDICTING CORONARY DISEASE FROM ECG SIGNALS, filed Jul. 23, 2020.

BACKGROUND

Approximately seven million Americans undergo emergency cardiac triage each year and the length of time to reach a final coronary diseases diagnosis is 8 to 72 hours. Also, approximately 40% of patients receive unnecessary coronary catherization, and 55-85% patients are considered to be over treated. Despite these measures, 2-6% of sick patients are discharged without treatment. Nearly 4 million cardiac catheterizations are performed annually in United States hospitals alone, with one in ten discharges having undergone coronary arteriography. Of these procedures, it is found that over 60% of them find patients with non-obstructive coronary artery disease—which is surprising as this is an invasive test reserved for the highest risk patients. Tests to indicate coronary disease, and thus need for cardiac catheterization, are generally accurate to an average of about 85%; meaning patients are sent for invasive catheterization with significant uncertainty of the need for such procedure. The innovation presented herein increases this accuracy and therefore provides for better estimate of procedure need, and it does so within seconds, and for a fraction of the cost of the hours-long testing currently used.

SUMMARY

The present invention is directed, in various aspects, to a medical diagnostic tool that help doctors (or other applicable health officials as the case may be) rapidly identify clinically significant cardiovascular disease and sort patients that need further testing from those that can be safely discharged. The software-based diagnostic tool can be trained through machine learning to enable users to better analyze and diagnose a patient's ECG signal. The software for the tool can be used with already cleared/approved ECG devices. The tool's software is able to accept input from any ECG device, regardless of device gain and sample frequency. The tool employs non-invasive technology that uses, for example, standard 12-lead ECG data to predict the presence, location, and severity of atherosclerotic cardiovascular disease (ACVD) and coronary artery disease (CAD). The results can be provided within second, as opposed to hours for current cardiac triage techniques. Plus, preliminary testing shows that the results are 95% accurate and the accuracy rate will improve with more data because the tool is trained through machine learning.

In one general aspect, the present invention is directed to a diagnostic tool that includes: a sensor for capturing at least one biosignal produced by a patient's heart; and a computer device that implements a deep neural network that is trained iteratively through machine learning to generate a prediction about a heart condition of the patient. After the deep neural network is trained, the computer device is configured to: convert the at least one biosignal to a multi-dimensional input matrix for the deep neural network generated from a number (N) of biosignals captured by the sensor, where each of the N biosignals is at least "T" seconds, and where T is at least one second and N is greater than 1; and process the multi-dimensional input matrix through the deep neural network. The output of the deep neural network from processing the multi-dimensional input matrix corresponds to the prediction about the heart condition of the patient.

In another general aspect, the present invention is directed to a method including: training, with a computer system, iteratively through machine learning, a deep neural network to make a prediction about a heart condition of a patient; and after training the deep neural network: capturing, with a sensor, at least one biosignal produced by a patient's heart; converting, by the computer system, the at least one biosignal to an input matrix for the deep neural network, wherein the input matrix includes a multi-dimensional matrix generated from a number (N) of biosignals of at least "T" seconds (where T is at least one second and N is greater than 1); and processing, by the computer system, the multi-dimensional input matrix through the deep neural network. The output of the deep neural network from processing the multi-dimensional input matrix through the deep neural network corresponds to the prediction about the heart condition of the patient.

In another general aspect, the present invention is directed to a computer system including one or more processor cores, wherein the one or more processor cores are configured to: train, iteratively through machine learning, a deep neural network to make a prediction about a heart condition of a patient; and after training the deep neural network: receive, from a sensor, at least one ECG signal produced by a patient's heart and captured by the sensor; convert the at least one ECG signal to an input matrix for the deep neural network, wherein the input matrix includes a multi-dimensional (or multi-axis) matrix generated from N ECG signals of at least T seconds, where T is at least one second and N is greater than 1; and process the input matrix through the deep neural network, wherein an output of the deep neural network from processing the input matrix through the deep neural network corresponds to the prediction about the heart condition of the patient.

The present invention, in various embodiments, provide many benefits over prior art systems. First, as described herein, the diagnostic tool can accurately and rapidly detect coronary diseases of a patient based on, for example, ECG signals of the patient. Second, the diagnostic tool can provide those accurate and rapid results even if not all twelve ECG leads are used on the patient. These and other benefits of the present invention will be apparent from the description to follow.

FIGURES

Various aspects of the present invention are described herein by way of example in connection with the following figures.

Figure 1:
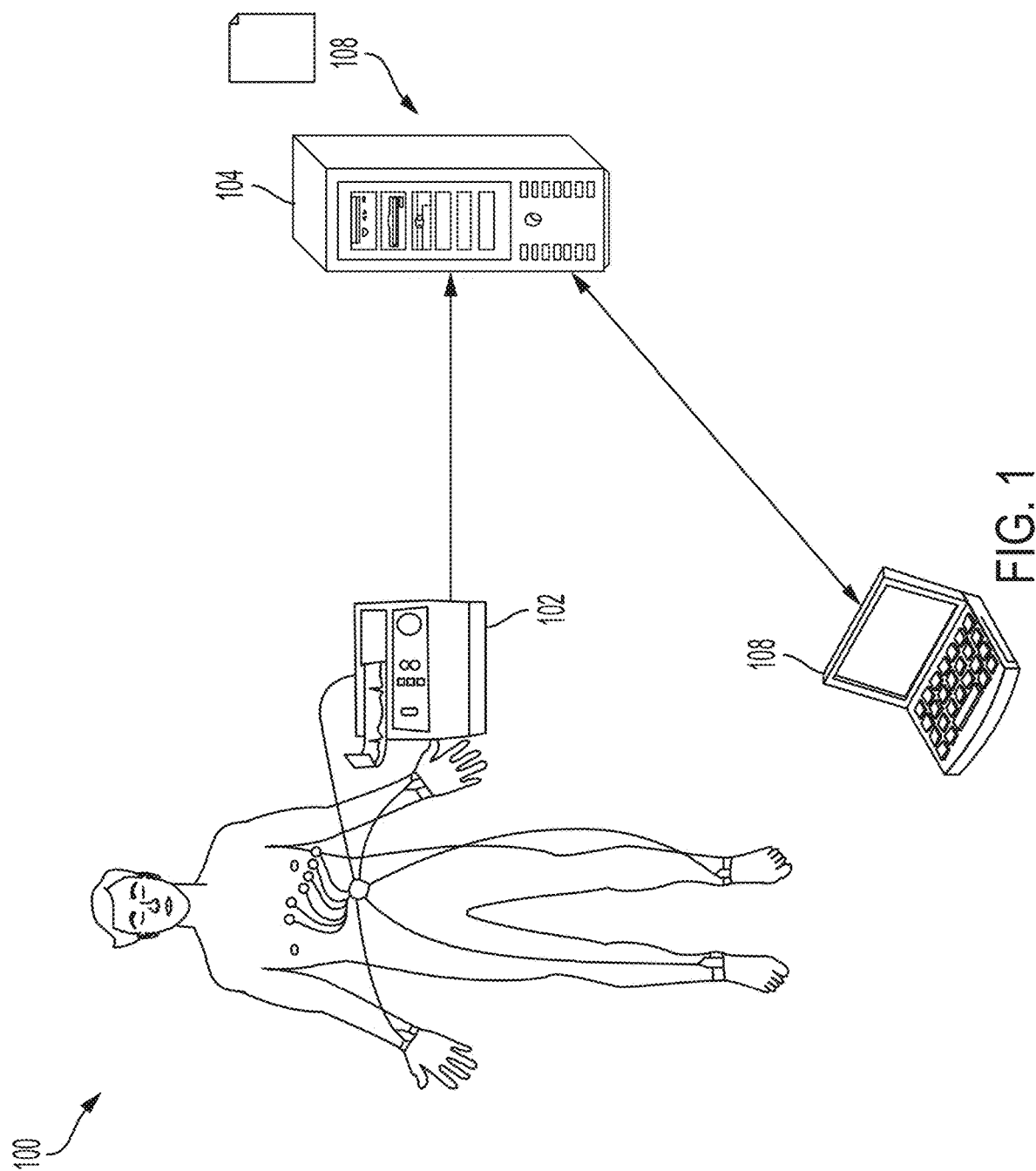
FIG. 1 is diagram of a medical diagnostic tool according to various aspects of the present invention.

FIGS. 5A-B and 6A-B depict visualizations generated by the medical diagnostic tool of FIG. 1 according to various aspects of the present invention.

Figure 7:
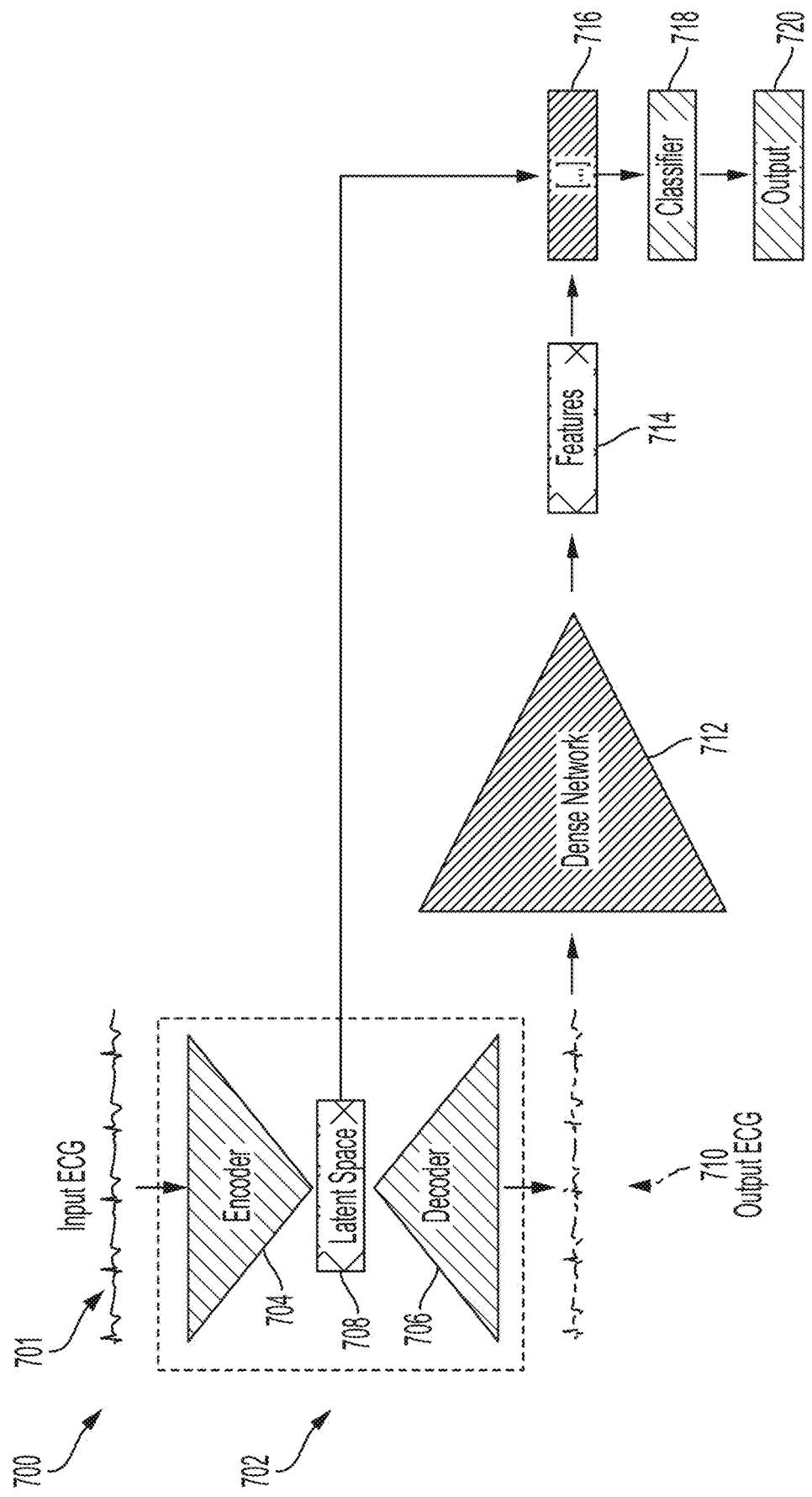

FIG. 7 is a diagram that depicts the neural model of the medical diagnostic tool of FIG. 1 according to various aspects of the present invention.

Figure 8:
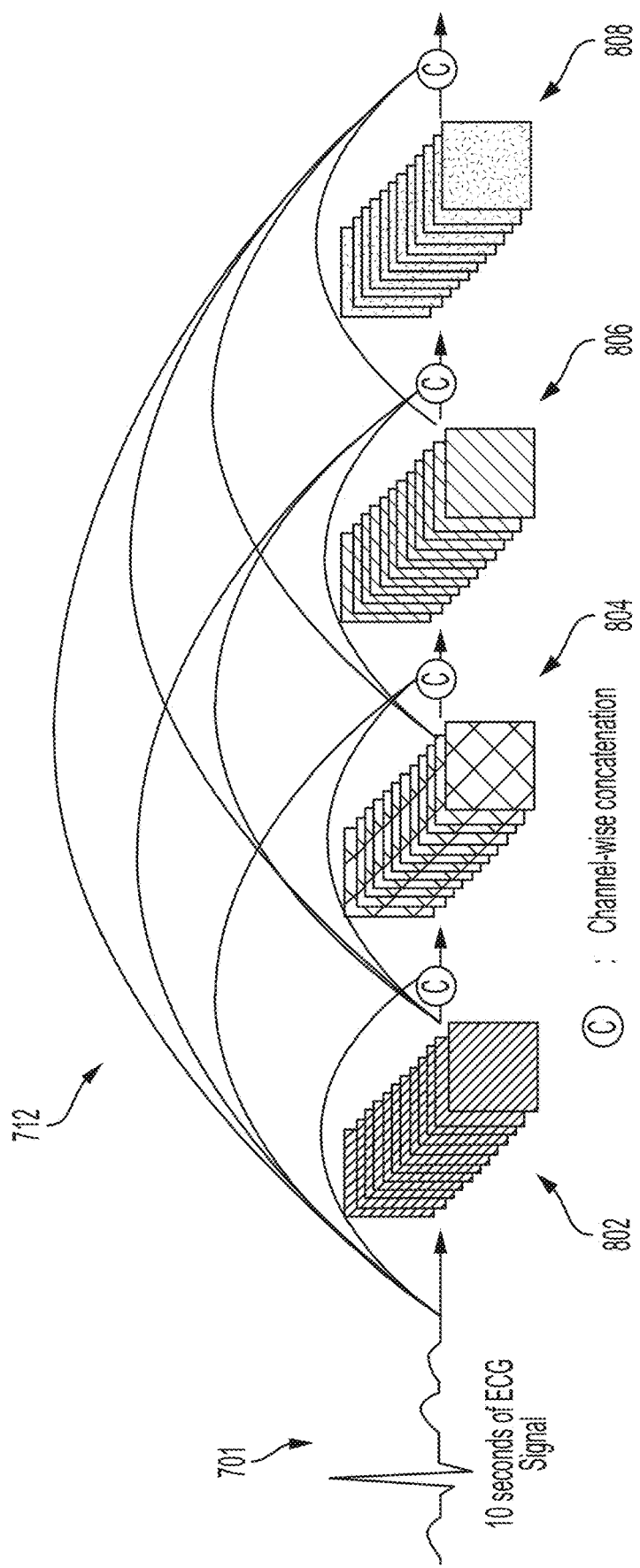

FIG. 8 depicts a densely connected convolutional network that can be used as part of the neural model of the medical diagnostic tool of FIG. 1 according to various aspects of the present invention.

Figure 9:
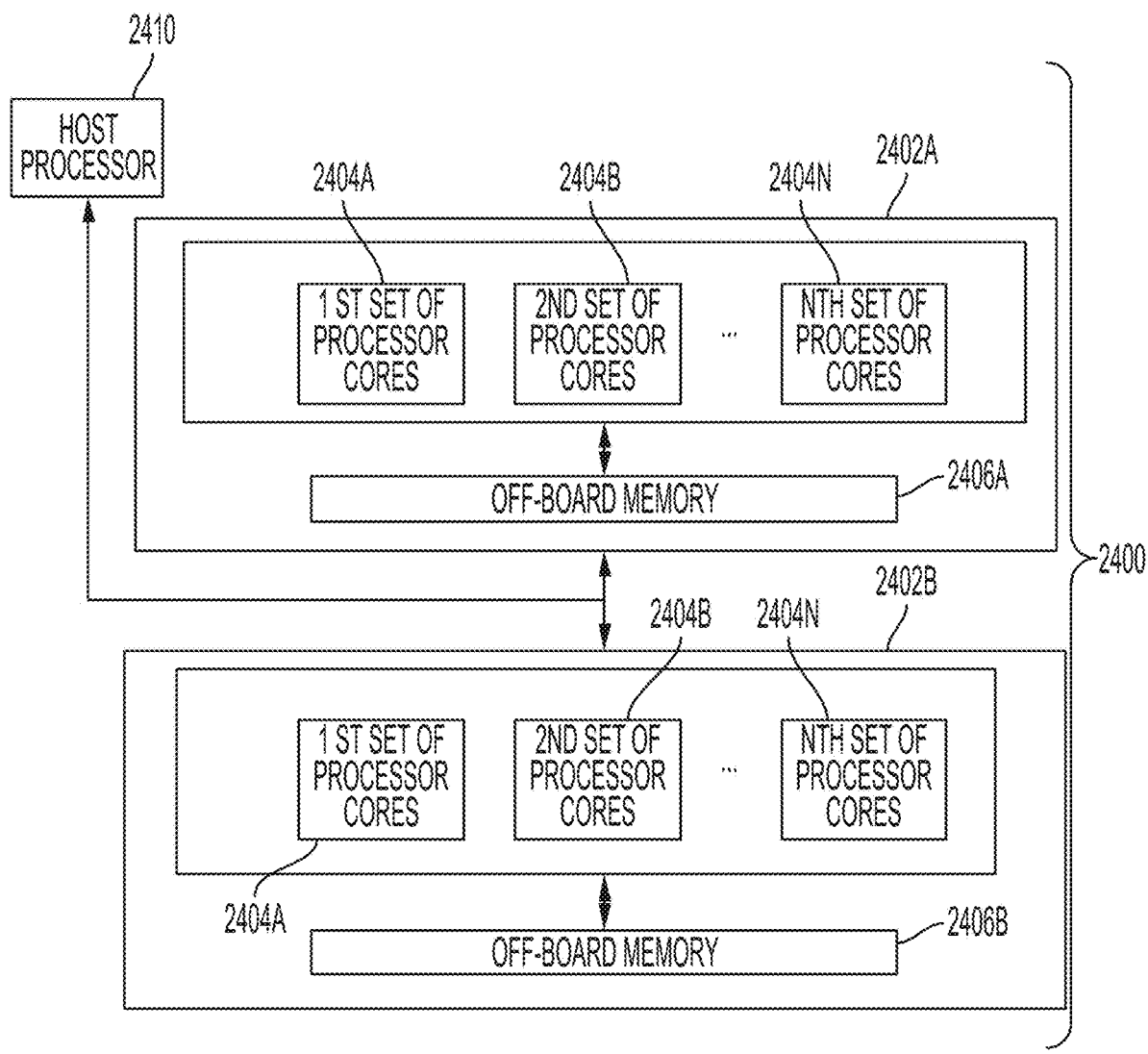

FIG. 9 is a block diagram of the computer device of the medical diagnostic tool of FIG. 1 according to various aspects of the present invention.

DESCRIPTION

The present invention is directed, in various aspects, to a medical diagnostic tool 100 for identifying clinically significant cardiovascular disease in a patient 101. In various aspects, the diagnostic tool 100 includes, as shown in FIG. 1, at least one sensor configured to capture biosignals associated with the patient. For example, the sensor 102 of FIG. 1 includes one or more leads of an ECG machine. Although the non-limiting aspect of FIG. 1 includes an ECG machine with one or more leads, it shall be appreciated that the sensor 102 can include any number of devices configured to capture any number of biosignals associated with the patient. For example, in other non-limiting aspects, the sensor 102 can include an electroencephalogram (EEG) machine. In still other non-limiting aspects, the sensor 102 can include a wearable device (e.g., a smart watch, a smart ring, a smart phone, or smart glasses, etc.) configured to generate either ECG or EEG signals. HEARTio. Furthermore, the sensor 102 can include any number of leads. According to the non-limiting aspect of FIG. 1, the sensor 102 could be a conventional 12-lead ECG machine, although other types of machines with any number of leads could be used. The sensor 102 can be communicably coupled to a back-end computer device 104, sometimes referred to herein as a "HEARTio computer." The computer device 104 includes modules 108 trained through machine learning to identify the existence (or non-existence) of one or more clinically significant cardiovascular diseases based on the ECG data from a patient.

The HEARTio computer 104 stores and executes a software program 108 that analyses a patient's biosignals (e.g., 12-lead ECG data) and outputs a predicted level, severity, and localization of coronary stenosis or other coronary diseases that the software is trained, through machine learning, to identify. The ECG data can be input, for example, to computer device 104 in the following ways: (1) Direct input of digital data points in a patient dataset via the hospital infrastructure; (2) Manual input of a digital signal file through an email client; (3) Manual input of a digital signal data via a dashboard provided by the computer device 104; and/or (4) Manual input of an biosignal waveform (non-digital signal such as a pdf or image) via a dashboard. For this last option, the computer device 104 can transform the non-digital signal into a set of a digital signal data. The computer device 104 could have a direct wired network (e.g., an Ethernet) or wireless (e.g., WIFI) connection to the computer device 104. Also, the computer device 104 could be on the cloud, in which case the biosignal data from a patient is uploaded to a database on the cloud, which database the computer device 104 can access to analyze the patient's biosignal data to make the diagnosis.

The software program 108 can include one or more neural models and, after input of biosignal data, the data is pushed through the neural model(s), sometimes referred to herein as a "HEARTio neural model" as shown in FIG. 1, implemented by the software 108 of the HEARTio computer 104. In that connection, the HEARTio neural model 108 can be a fixed graph that has a very specific set of instructions for how to process the input data. Then HEARTio computer 104 can separate the biosignal data into more than, for example, 100 distinct layers of the graph (or neural network) by applying a specific set of mathematical operations to the data exiting the preceding layer in the neural graph. The final layer of the HEARTio neural model 108 preferably provides an array of probabilities for the question being asked (Is this biosignal representative of coronary stenosis? How severe is this coronary stenosis? What is the location of the coronary stenosis? etc.)

The difference between a normal software program and the HEARTio neural model 108 is that the set of instructions for the HEARTio neural model 108 is not determined by a physician, programmer, or expert, but by the HEARTio computer 104 itself. A typical software program implements a known flow of information through a fixed set of code to perform processes on the data, but those processes are designed by the programmer. With the diagnostic tool 100 of the present invention, the determination of these instructions is done algorithmically, meaning the HEARTio computer 104 itself determines what mathematical operations are used to operate on data exiting one layer of the graph and being delivered to the next layer. A training set of data is used to train the neural model 108 using, for example, supervised, unsupervised, and/or semi-supervised training. The graph is initially set up to use a randomly generated set of instructions to deliver the next layer of data from the preceding layer, with the first layer being the "training set" of biosignal data, singularly, for each patient in the "training set".

The biosignal data in the training set is pushed through the various layers of the graph, with its mathematical operations between each layer, and then, after the last layer, the initial set of answers are recorded. In supervised training, the answers are known, as part of the iterative training, the answers produced by the model 108 can be compared to the actual answers/results associated with the training data. If the experimental results and the expected results are far away in magnitude, then the instructions representing the mathematical operations between the layers is adjusted (done by the HEARTio computer 104 according to an algorithm) to move the model 108 closer to a set of operations that may offer better results at the end of the last layer. If the distance between the real answer and the answer computed by the combination of the all the operations between the numerous layers in the graph is minimal, possibly only the operations between lower levels are adjusted. This process is repeated, over and over, until the congruence between the experimental results and the expected results are satisfactory, at which point the model of mathematical operations between the layers can then be applied on additional patient biosignal data.

After training has concluded, the final graph (set of mathematical operations acting between the various layers of the model) is fixed and ready to be used to process biosignal data that was not included in the training set. The process of inputting new data to the neural model 108 is called "testing". The main advantages to allowing the computer 104 to determine the optimal set of instructions are that a) it can revise the instructions and evaluate the results much more quickly than with human involvement, b) it can use a much more complicated instruction set than can be envisioned by humans, and c) it can update the instructions with the acquisition of new data to get, theoretically, more and more accurate results with more and more experience. Thus, the biosignal neural model 108 will adapt to novel data, leading to more accurate analysis of biosignal data with respect to coronary stenosis or other monitored-for conditions as the case may be.

Figure 2:
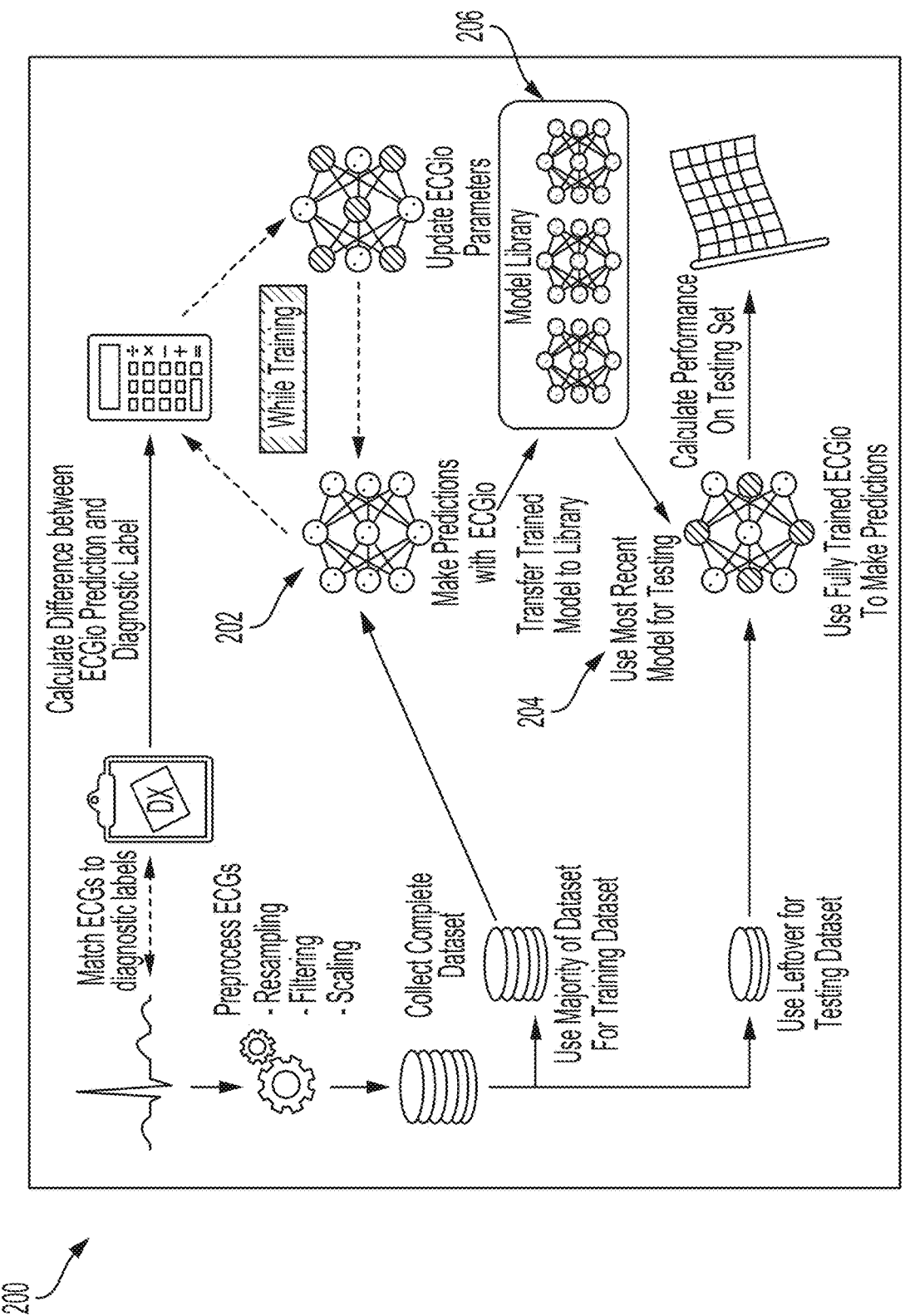
FIGS. 2 and 3 depict a process for training and validating a neural model of the medical diagnostic tool of FIG. 1 according to various aspects of the present invention.

FIG. 2 depicts the training and validation processes 200 in more detail. The patient cohort is split into two groups: a "training set" 202 and a "testing set" 204. Generally accepted deep learning practice is to utilize greater than 90% of the patient cohort for the training set 202 and the remainder to validate the accuracy statistics of the model 206. The programmer may also manually set the hyperparameters, for the training, which are parameters unrelated to the training set but will impact the training environment (e.g., learning rate, label smoothing, dropout rate). Once the patient cohort is split and before training begins, the model randomizes the model 206 parameters it will refine to build the statistical dependencies between input and output. Over time the model 206 improves upon these parameters utilizing a process known as gradient descent, in which each of the parameters searches for local minimums of a loss function (the measure of how different the prediction is from the actual value).

Figure 3:
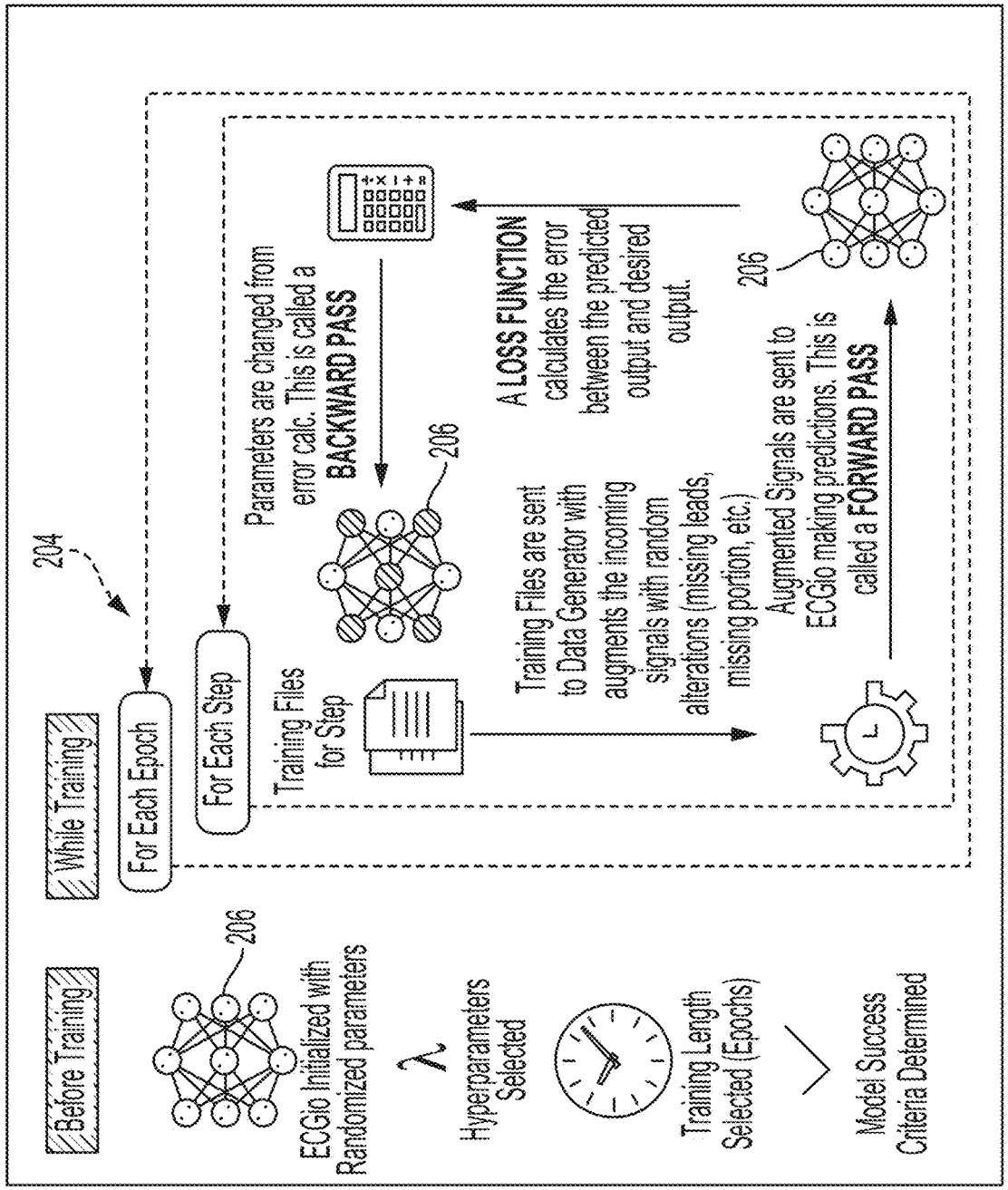

Training the model 206 is iterative (as shown in FIG. 3). The number of epochs (a measure of how many forward and backward passes the model 206 makes as part of the iterative gradient descent training), and the number of steps per epoch (a measure of how many data points are evaluated within the epoch) may be set by the programmer. In each epoch, a training set is randomly pulled from the training cohort 204. The model 206 then makes predictions about the patient based on patient biosignals, trying to identify important parameters that make the correct diagnosis. Once the forward pass (forward propagation) is complete, the predictions are sent to the loss function, which compares the predictions against the actual patient conditions and determines the overall error. This error then gets back-propagated through the model 206 and helps adjusts parameters to correct for the model 206 error.

After all the epochs are complete, the final model 206 is considered "trained" and that model is passed to testing. This trained model 206 is then given the previously defined "testing set", which it has never seen, to predict patient conditions. These predictions are compared to the actual patient outcomes and these results are reported as model 206 performance (usually in terms of sensitivity, Positive Predictive Value (PPV), and F-1 score).

The longer the duration of the input 208 fed into the HEARTio neural model 206 generally the better. Preferably, the duration of the input 208 should be at least one second. In various aspects, the input 208 (FIG. 4) that is fed into HEARTio neural model 206 is more than 5 seconds and less than 15 seconds, such as ten seconds, of standard ECG signals (or other biosignals as the case may be) and can be anywhere from one to twelve leads. The model 206 output 210 (FIG. 4) can include, for example, in six different but related areas: beat classification, rhythm classification, Myocardial Infarction (MI) classification, Major Adverse Cardiovascular Events (MACE) prediction, and CAD severity classification. Of course, the output 210 can include any other information associated with the heart of the patient 101 (FIG. 1) as determined by the model 206. Unlike most current biosignal interpretation software, which simply monitors basic beats, rhythm, and MI detection, the HEARTio computer 104 (FIG. 1), with its HEARTio neural model 206, can be trained to detect, for example, 17 different and highly clinically relevant beat types, 17 different and highly clinically relevant rhythm types, and five different and highly clinically relevant MI types. The HEARTio computer 104 (FIG. 1) can provide this improvement through in MACE prediction, and CAD severity classification prediction. The HEARTio neural model 206 can be trained to predict a patient's risk for a MACE, determine that patient's current level of CAD, and localize stenosis in the patient's coronary arteries. The outputs that the HEARTio neural model 206 can be trained, in various aspects, to detect are listed in Table 1 below.

TABLE 1

| Beats<br>Possible Labels | Rhythm<br>Possible Labels |
|---|---|
| Aberrated atrial premature beat | Atrial fibrillation |
| Atrial escape beat | Atrial flutter |
| Atrial premature beat | First heart block |
| Fusion of paced and normal beat | Idioventricular rhythm |
| Fusion of ventricular and normal beat | Nodal (A-V junctional) rhythm |
| Left bundle branch block beat | Noise |
| Nodal (junctional) escape beat | Normal sinus rhythm |
| Nodal (junctional) premature beat | Paced rhythm |
| Non-conducted P-wave (blocked APC) | Pre-excitation (WPW) |
| Normal beat | Second heart block |
| Paced beat | Supraventricular tachyarrhythmia |
| Premature ventricular contraction | Ventricular bigeminy |
| Right bundle branch block beat | Ventricular flutter |
| Supraventricular premature or ectopic beat (atrial or nodal) | Ventricular tachycardia |
| Unclassifiable beat | Ventricular trigeminy |
| Ventricular escape beat | Atrial bigeminy |
| Ventricular flutter wave | Sinus bradycardia |

| MI<br>Possible<br>Labels | MACE Risk<br>Possible<br>Labels | Severity<br>Possible<br>Labels | Localization<br>Vessel Blockage<br>Percentage |
|---|---|---|---|
| Acute MI | None | Low/Mild | LAD % |
| Prior MI | MI | Moderate | LCX % |
| NSTEMI | Stroke | Severe | LM % |
| Prior CABG | Syncope | | RCA % |
| Prior PCI | | | |

Figure 4:
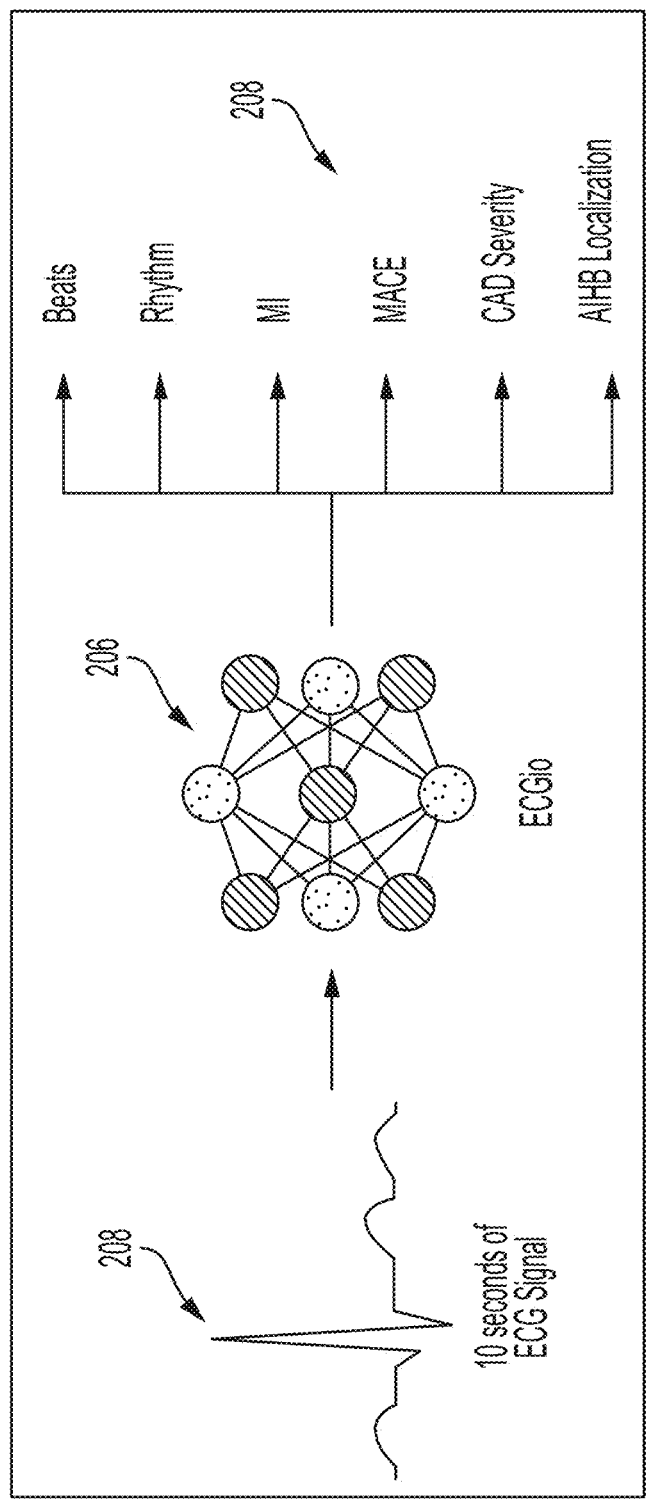
FIG. 4 depicts outputs of the neural model of the medical diagnostic tool of FIG. 1 according to various aspects of the present invention.
Figure 5A:
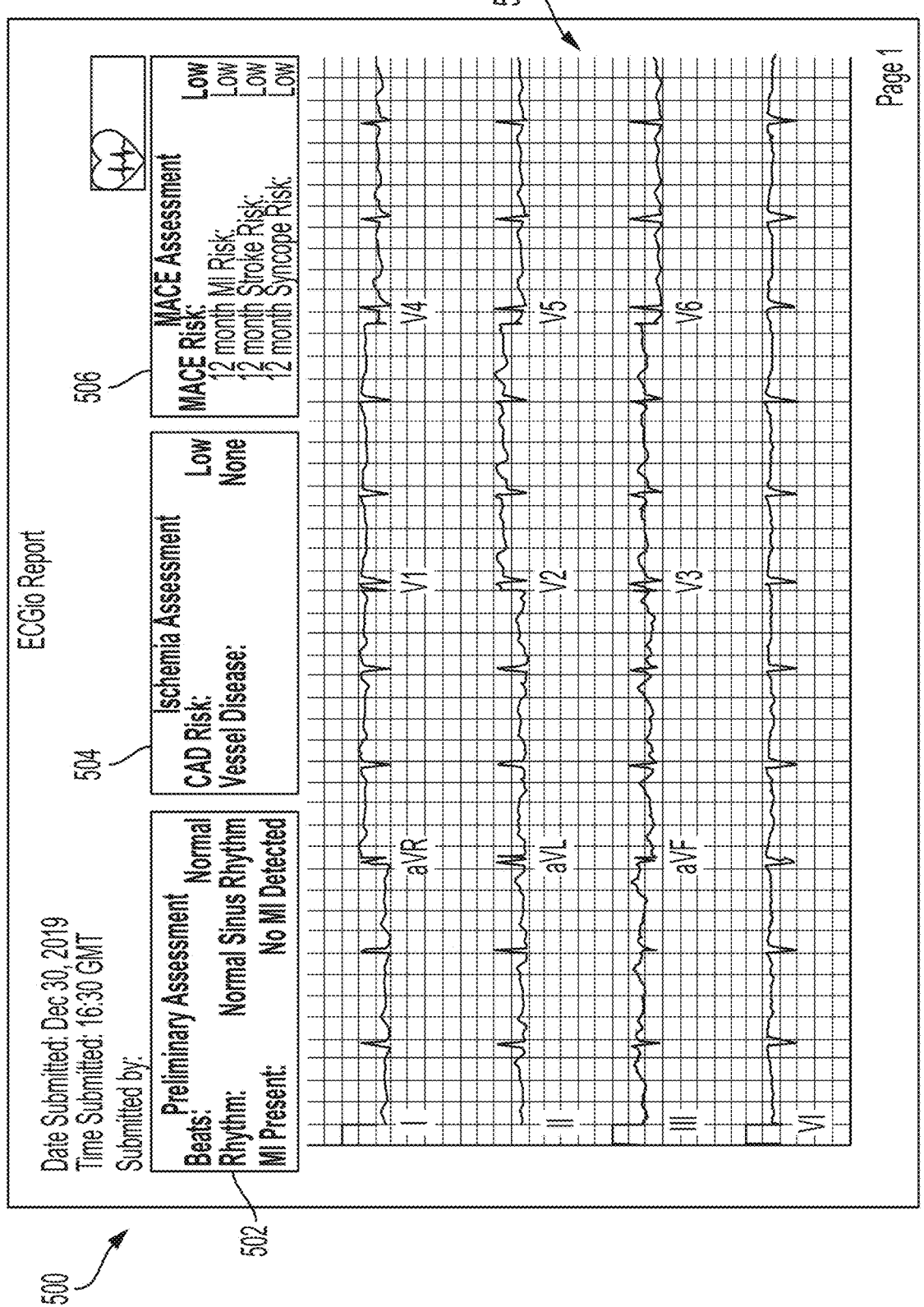
Figure 5B:
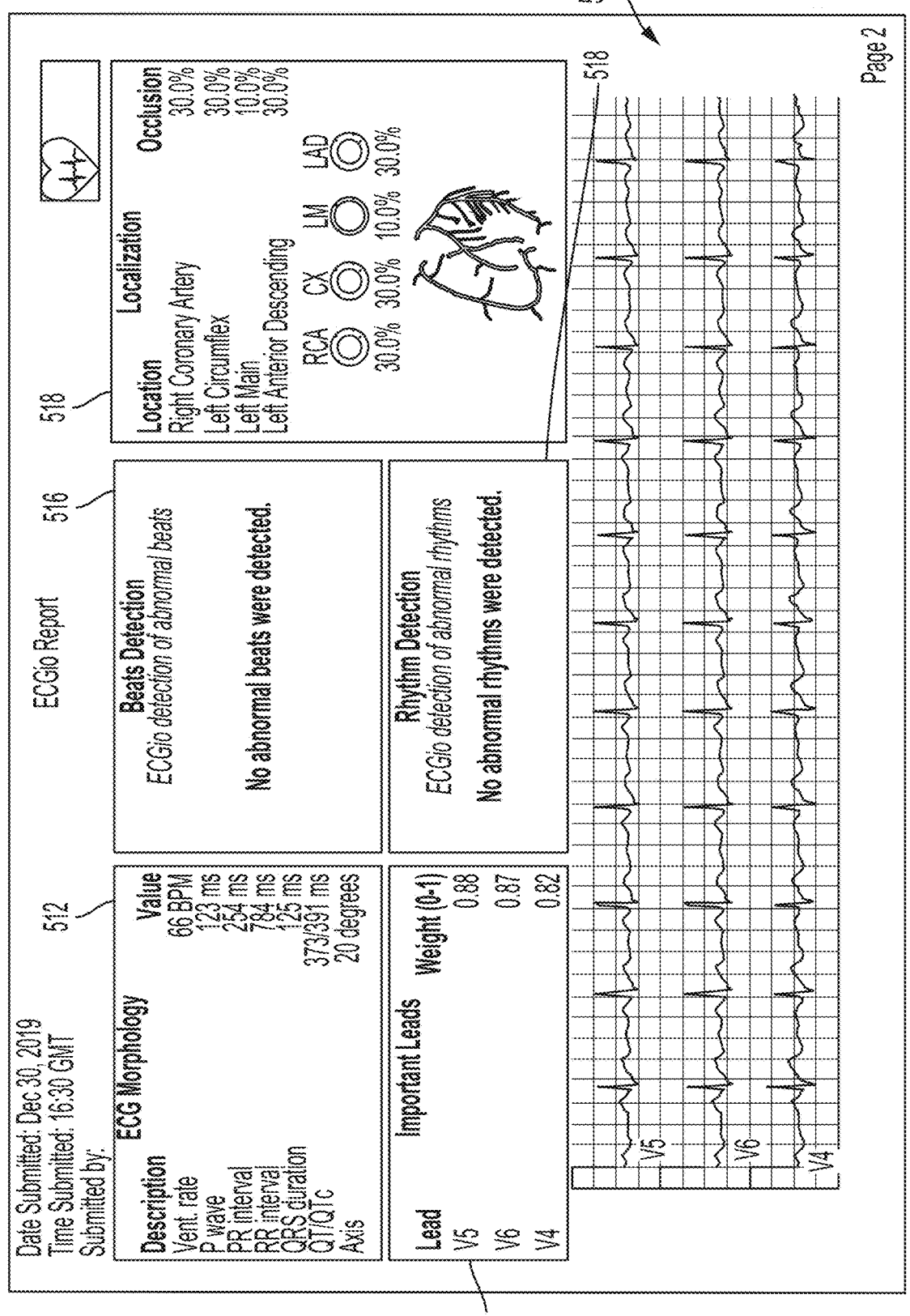

The HEARTio computer device 104 (FIG. 1) may also be programmed to generate graphical displays that display the results of its analysis, which can be accessed via a display 108 (FIG. 1) communicably coupled to the computer device 104 (FIG. 1). For example, the graphical output displays could be displayed on a monitor of the HEARTio computer device or on another device, e.g., the user device 108 shown in FIG. 1, that is in data communication with the HEARTio computer device 104 (FIG. 1). For example, the HEARTio computer device 104 (FIG. 1) could include a web server that serves the results via web pages to the user device 108 (FIG. 1). FIGS. 5A-B and 6A-B show example graphical output displays 500, 510 that can be generated by the HEARTio computer device 104 (FIG. 1). FIG. 5A is an example graphical display 500 that could be displayed, for example, to an emergency medicine physician or a triage nurse. The example 500 of FIG. 5A can include a preliminary assessment 502 of the patient's heart, an ischemia assessment 504 include an estimated risk of CAD, and a MACE assessment 506, all of which are determined by the trained model 206 (FIGS. 2-4). The display 500 of FIG. 5A can be used by an ED physician. It includes fields that convey: whether the patient's beats and rhythms are normal or not and whether MI is present 502; an ischemia assessment 504, such as whether there is CAD risk or whether vessel diseases was detected; and a MACE assessment 506, including the risk of 12 month MI, 12 month stroke, and 12 month syncope. The biosignal (e.g., ECG, EEG, etc.) waveforms 508 at the bottom of FIG. 5A show most important biosignal leads that contribute to the severity distinction as determined by the HEARTio neural map. A second graphical display, such as the display 510 of FIG. 5B, can include fields that show biosignal morphology 512, important biosignal leads 514, whether abnormal beats were detected 516, whether abnormal rhythms were detected 518, occlusion amounts (e.g., percentages) of various arteries 520, as well as biosignals from various leads (e.g., the important leads) 522. For example, as shown in FIG. 5B, the output visualization can show the percent lesion blockage 520 within each of the 4 major coronary arteries. If the blockages are low, moderate, or high, they can be shaded differently (e.g., green, yellow, red).

Figure 6A:
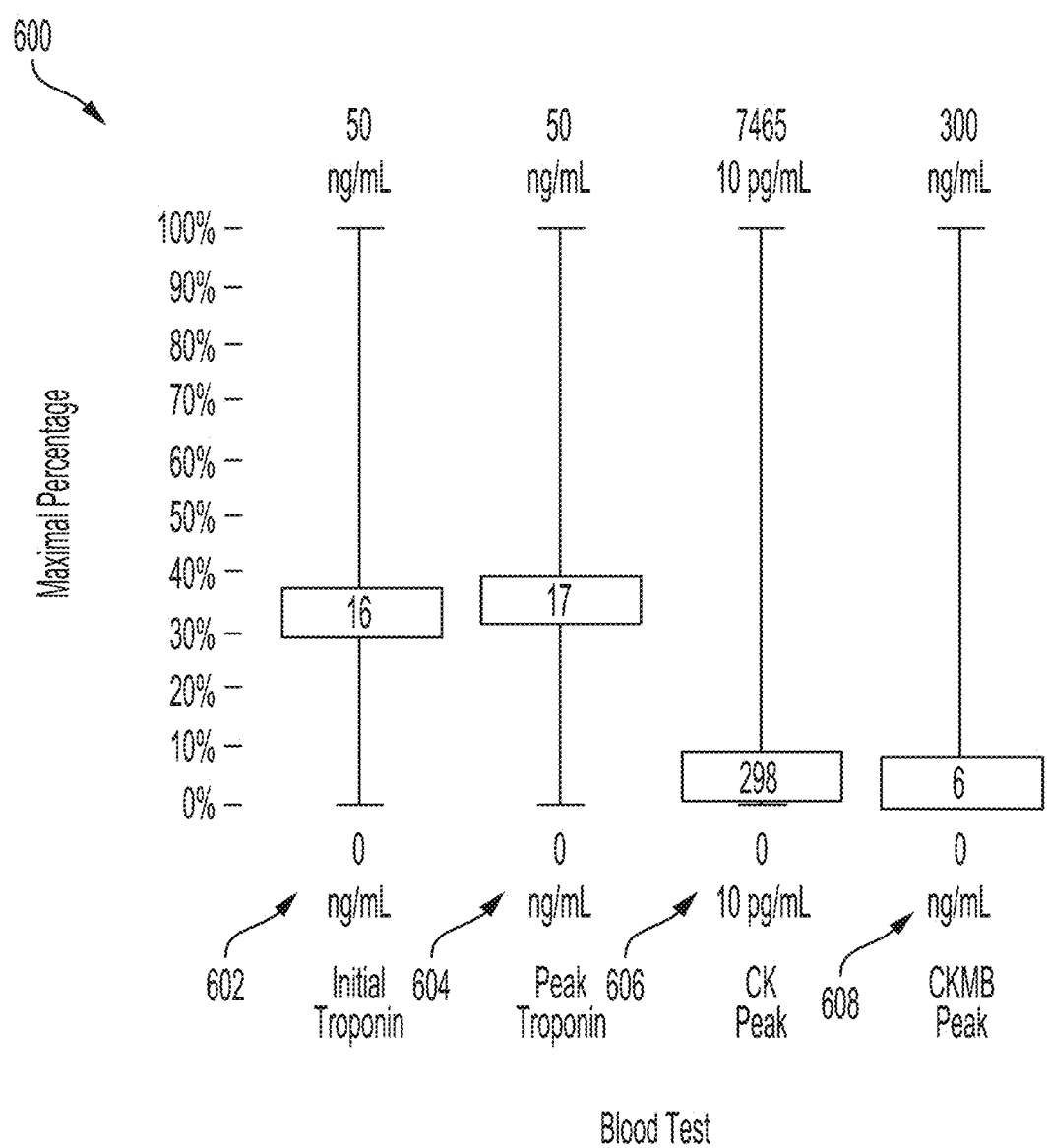
Figure 6B:
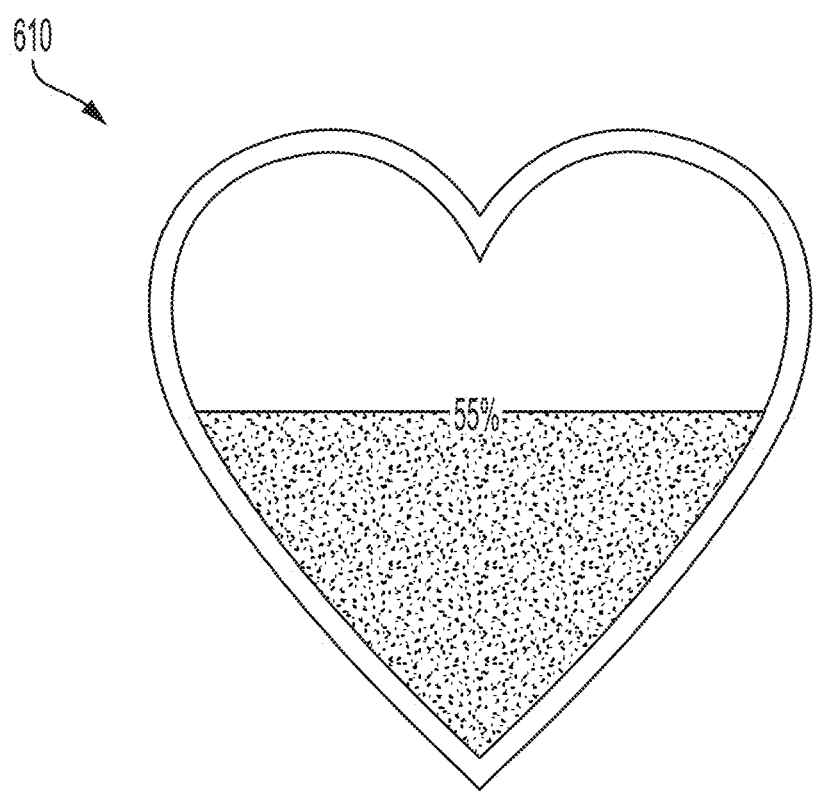

FIGS. 6A and 6B shows other graphical visualizations 600, 610 that can be provided by the computer system 104 (FIG. 1). The visualization 600 of FIG. 6A shows the predicted levels of 4 different blood tests 602, 604, 606, 608 that the HEARTio model 206 (FIGS. 2-4) has generated outputs for. Once again, the graphical visualization 600 can use color coding to visually communicate information to a using technician. For example, if the levels are low the bars can be green; if they are moderate it will be yellow; and if they are high it will be red (or some other color coding). The visualization 610 of FIG. 6B shows the level of ejection fraction. The higher the level the heart graphic fills up. If the EF is low, the color in the graphic can be yellow and, if even lower, red (or some other color coding).

In various aspects, the input to HEARTio neural model 206 (FIGS. 2-4) is a tensor with 4 axes: batch, signal, lead, and channel. The batch axis refers to the total number of biosignal that are being processed at the same time; if a single biosignal is being evaluated then the batch axis size would be 1. The signal axis represents the discrete numerical signal value for 10 seconds of time; in various aspects, the size of this axis is nonvariable and is 1000. The lead axis represents the standard 12 leads that include a resting biosignal; and this axis can be nonvariable in certain aspects. The channel axis is preferably nonvariable as well and set to 1. This axis is used as a convenience for convolutional processing. Overall a biosignal can be represented by 12,000 double (float32) values. Many biosignal algorithms are based on the concept of rule-based analysis, meaning that are rules set in stone determined by expert opinion or rudimentary analysis. This type of analysis usually requires the manual input of demographic information such as sex, age, race, family history. The HEARTio neural model does not require any further input than the biosignal represented in tensor form and can be blind to any other information.

The tensor form biosignal, for example, can include a conventional ECG with anywhere from 1 to 12 leads organized as shown in Table 2 below. Alternatively, the tensor form biosignal can include a conventional EEG with anywhere from 1 to 19 leads. If a lead does not exist in the original signal it is replaced by a series of zeros. If the tensor form biosignal was extracted from an image or PDF there might a series of zeros in different parts of various leads.

TABLE 2

| ECG leads and their respective index in the lead axis | |
| --- | --- |
| Lead | Lead Axis Index |
| I | 0 |
| II | 1 |
| III | 2 |
| aVR | 3 |

TABLE 2-continued

| ECG leads and their respective index in the lead axis | |
| --- | --- |
| Lead | Lead Axis Index |
| aVL | 4 |
| aVF | 5 |
| V1 | 6 |
| V2 | 7 |
| V3 | 8 |
| V4 | 9 |
| V5 | 10 |
| V6 | 11 |
| X | 0 |
| Y | 1 |
| Z | 2 |

To create a biosignal in tensor form the following steps may be followed. First, clip a biosignal such that it represents (for example) 10 seconds and is in the form N×M, where M is the number of the leads and N is the number of samples. N is equal to the sampling rate of the biosignal multiplied by 10. Second, using fast Fourier transform (FFT), resample N to 1000, in effect reducing the sampling rate to 100 Hz. Third, bandpass Butterworth filter with a passband starting at 2 Hz and extending to 40 Hz. This will try to make sure only the information within this band of frequencies are retained while others are removed. Fourth, each filtered signal can be scaled by the following formula:

$$f(x) = 2\frac{x - \min(x)}{\max(x) - \min(x)} - 1$$

This will make every value between −1 and +1. Fifth, any NaN value can be converted to 0. And sixth, each signal can be detrended such that the isoelectrical portions of the biosignal are 0. After this level of preprocessing there still might be signals, or leads of signals, that do not have a reasonable amount or degree of usable information. In that case, there is a series of steps that are used in training the neural model that can also be used to disregard the signals without usable information.

The outputs of HEARTio neural model can fit into the following major archetypes, where each index of the output array represents a class or category:
  1. Reconstruction: Array is the form of a reconstructed biosignal.
  2. Scaled-Continuous: Values in this output array are continuous but scaled to be between 0 and 1.
  3. Multi-Class: Each output array can only contain 1 value of 1, all other values are 0. There is only 1 class that be present.
  4. Multi-Label: Each output array can have multiple values of 1. Each class can be present or absent.

Table 3 below shows an example macro listing of output of the HEARTio neural model and the shaped associated with each output.

TABLE 3

| Output Name | Length | Type |
| --- | --- | --- |
| Reconstruction ECG | {1000, 12, 1} | Reconstruction |
| Coronary Blockage % | 4 | Scaled-Continuous |
| MI & History | 5 | Multi-Label |
| Abnormal Beats | 17 | Multi-Label |
| Abnormal Rhythms | 17 | Multi-Label |

TABLE 3-continued

| Output Name | Length | Type |
|---|---|---|
| SPECT | 20 | Scaled-Continuous |
| MACE Risk | 4 | Multi-Class |
| CAD Severity - Overall | 3 | Multi-Class |
| CAD Severity - Leads | 3 | Multi-Class |
| Coronary Binary Blockage | 4 | Multi-Label |
| Blood Test Predictions | 4 | Scaled-Continuous |
| Complications | 4 | Multi-Label |
| Ejection Fraction | 1 | Scaled-Continuous |
| Disease | 1 | Multi-Label |
| Conduction Disorders | 11 | Multi-Label |
| Hypertrophy | 5 | Multi-Label |
| Location of MI | 14 | Multi-Label |
| Morphology | 15 | Multi-Label |
| ST-T Changes | 13 | Multi-Label |
| Ejection Fraction Binary | 1 | Multi-Label |
| FFR | 1 | Scaled-Continuous |
| FFR Binary | 1 | Multi-Label |

Table 4, in Appendix A hereto, shows the indexes within each major category according to various aspects of the present invention.

In various aspects, the basis of HEARTio neural model 206 (FIG. 2) is the development and training of three distinct models that work in concert to provide information and thoroughly analyze biosignals. The steps of the HEARTio neural model 206 (FIG. 2), once trained, are as follows, with reference to FIG. 7:

1. A biosignal 701 is input and processed through an encoder 704 which performs a lossy compression
2. The minimized representation of this lossy compression, called the latent space 708, serves as input to two layers: a concatenation layer 716 (used later on), and a decoder 706
3. The decoder 706 converts the latent space representation 708 back into the tensorform biosignal 710
4. The tensorform biosignal 710 is input into a Dense network 712 to produce a feature vector 714
5. The feature vector 714 and the latent space 708 are concatenated to form one feature vector 716, which is used as input to a classifier 718
6. Outputs 720 from the classifier 718 are collected at the end The encoder 704 and decoder 706 form an autoencoder 702. The autoencoder 702 can use information about the biosignal and any extra leads to remove non-significant noise from the biosignal in its reconstruction. The autoencoder 702 can also detect with biosignal leads are empty and, in various aspects, fill them in accordingly using information from existing leads. For example, where there is just one existing lead, the autoencoder 702 can generate the 11 other, missing leads so that there are 12 signals to be used by the dense network 712. The autoencoder 702 can also standardize the biosignals such that there is no artifact that is only related to one type of biosignal lead or patient.

In various aspects, the encoder 704 can include approximately 13.5 million total parameters, with approximately 99.97% of them being trainable parameters (with the remainder being non-trainable parameters), as shown in Table 5 at Appendix B. Table 6 at Appendix C shows, in one aspect, a detailed description of each type, output shape, and number of parameters associated with each later of the decoder of FIG. 7. Table 7 below shows, in one aspect, a detailed description of each type, output shape, and number of parameters associated with each layer of the overall autoencoder 702. The encoder 704 can be configured to perform a lossy compression of the at least one biosignal captured by the sensor 102 (FIG. 1), thereby producing a latent space representation 708 as an output of the lossy compression. The decoder 706 receives the latent space representation 708 as an input from the encoder 704 and can be configured to convert the latent space representation 708 into a tensorform signal output 710 provided to the DenseNet neural network 712.

TABLE 7

Model: "Autoencoder"

| Layer (type) | Output Shape | Param # |
|---|---|---|
| input 3 (InputLayer) | (None, 1000, 12, 1) | 0 |
| Encoder (Model) | (None, 1024) | 13451936 |
| Decoder (Model) | (None, 1000, 12, 1) | 13324801 |
| lead adjuster 1 (LeadAdjusted) | (None, 1000, 12, 1) | 1 |

Total params: 26,776,738
Trainable params: 26,746,018
Non-trainable params: 30,720

The DenseNet 712 shown in FIG. 7 may be implemented with a form of a deep neural network 712, including an input layer 802, an output layer 808, and one or more hidden layers 804, 806 between the input layer 802 and output layers 808 (see FIG. 8), where each layer includes at least node, and directed arcs between nodes. An output value for each node can be computed by the computer system according to an activation function for the node, where the inputs to the activation function for a node are weighted outputs of the node(s) having directed arcs to the node for which the activation value is being computed. The weights for the arcs and any applicable bias values can be learned parameters that are learned through the training. In various aspects, the dense network 712 shown in FIG. 7 can be implemented with a densely connected neural network (DenseNet) 712. In such a DenseNet 712, each layer obtains additional inputs from all preceding layers and passes own its own feature-maps to all subsequent layers. Concatenation 716 during forward propagation can be used, such as shown in FIG. 8, wherein the circle c's denote concatenation. Each layer 802, 804, 806, 808 can receive a "collective knowledge" from all preceding layers of the neural network 712. For example, after receiving the tensorform signal output 710 from the decoder 706 of the autoencoder 702, the DenseNet 712 can be configured generate a feature vector 714 based, at least in part, on the tensorform signal 710. The DenseNet 712 of FIG. 8 can include an input layer 802, a concatenation layer 804, a classifier layer 806, and an output layer 808. According to the non-limiting aspect of FIG. 8, the concatenation layer 804 can be configured to receive the feature vector from the input layer 802 and the latent space representation into a concatenated feature vector However, it shall be appreciated that in other non-limiting aspects, the DenseNet 712 can include these and any other layers configured to generate outputs that can produce meaningful predictions regarding the heart condition of the patient. In that case, the network 712 can be relatively thinner and compact, resulting in high computational efficiency and memory efficiency. Table 8 in Appendix D provides a detailed description of each type, output shape, number of parameters, and connections associated with each layer of the dense network according to one aspect of the present invention.

Table 9 in Appendix E provides a detailed description of the full neural network, including the encoder, decoder and dense network, according to various aspects of the present invention.

As mentioned above, the HEARTio neural model can be trained to work with all twelve leads of a standard 12-lead ECG machine or with less than all of the leads downs to just one lead. During training, the following adjust adjustment process can be used to adjust the training data to train the HEARTio neural model to work with 1 to 12 leads.

If the training data has 12 leads:
    X1% chance of leaving the signal as is
    X2% chance of randomly choosing 1 lead
    X3% chance of randomly choosing up to 11 leads
    X4% chance of removing 75% of each lead
    where X1+X2+X3+X4=100%
If input ECG training data has greater than 1 but less than 12 leads
    Y1% chance of leaving the signal as is
    Y2% chance of randomly choosing 1 lead
    Y3% chance of randomly choosing up to N−1 leads
    where Y1+Y2+Y3=100%; and
If input ECG has only 1 lead, leave signal as is.

The autoencoder 702 (FIG. 7) may employ a reconstruction loss function to make that the autoencoder's 702 (FIG. 7) reconstruction remains as faithful to the input biosignal. The reconstruction loss function may be based on a squared difference between the fast Fourier transform (FFT) between the input lead 701 (FIG. 7) (if available) and the output lead 710 (FIG. 7) from the autoencoder 702 (FIG. 7). Values with 0s in the biosignal can be ignored and not considered. The loss can be average per input signal.

The loss function set forth below can be used by any output that is of the scaled-continuous variety. Input biosignals that contain −1 can be masked and ignored. Each of the gold-truth outputs can be stratified into, for example, 25 bins that are evenly distributed between 0 and 1. Each bin can be cycled through and the mean squared log error (MSLE) between the predicted and true arrays that correspond to a particular bin can be calculated. This can be performed for every index found in the scaled-continuous output. The loss can be averaged among all indexes and bins.

```
def weighed_stats_MSLE ( y_true ,y_pred ) :
    mask_true = K. c a s t (K. not_equal ( y_true , −1) , K. f l o a t x ( ) )
    num_true = K.sum( mask_true )
    nbins = 25
    indic e s = t f . histogram_fixed_width_bins ( mask_true * y_true , ¥
    [0 .0 , 1.0] , nbins = nbins )
    num_class = y_true . get shape ( ) . a s l i s t ( ) [ − 1]
    unique , = tf.unique (K. f l a t t e n ( i n d i c e s ) )
    unique = K.sum(K. c a s t (K. o n e s li ke ( unique ) , K. f l o a t x ( )
) )
    first_log = K. l o g (K. c l i p ( mask_true * y_pred ,
K. e p s i l o n ( ) , None ) + 1 . )
    second_log = K. l o g (K. c l i p ( mask_true * y_true ,
K. e p s i l o n ( ) , None ) + 1 . )
    mse = K. square (first_log − second_log)
    loss = 0 . 0
    for j in range ( nbins ) :
        inds = mask_true *K. c a s t (K. equal ( i n d i c e s , j ) ,
K. f l o a t x ( ) )
        for i in range ( num_class ) :
            loss += 1 . 0 / ( unique * num_class ) *K.sum(¥
            inds [ : , i ] * mse [ : , i ] ) / (K.sum( inds [ : , i ] ) +
K. e p s i l o n ( ) )
    return loss
```

Also, the loss function set forth below can be used by the any output that is of the multi-class variety. Input biosignals contain an index that is considered a dummy index. For example, CAD Severity—Overall, has 3 indexes that are correlated to the three possible mutually exclusive categories. The output can be given 4 indexes overall if a data point does not have a label for this output. During training if a biosignal does not have a label for the output, the dummy index is occupied, but with this loss function, the dummy index is ignored. The categorical cross-entropy is calculated and averaged along legitimate outputs. According to some non-limiting aspects, if the output does not have a corresponding label, the computer system 104 (FIG. 1) can create a label on the fly that corresponds to the output that did not previously have a corresponding label.

```
def f (y_true, y_pred ):
    sum_cols = K. c l i p (K.sum(y true , a x i s = 0 ) , 0 . 0, 1 . 0 )
    num_in = K.sum( sum cols [ 0 : mask_value ] ) + K. e p s i l o n ( )
    c_ce = K. c a t e g o r i c a l cross entropy ( y_true , y_pred )
    loss = 0 . 0
    for i in range ( mask value ) :
        inter mask = K. c a s t (K. equal (K. argmax (y_true) , i ) ,
K. f l o a t x ( ) )
        loss += 1 . 0 / ( num in ) *K.sum( inter_mask * c_ce ) ¥
        /(K.sum( inter_mask ) + K. e p s i l o n ( ) )
    return loss
```

The loss function below can be used by the any output that is of the multi-label variety. Input biosignals that contain −1 can be masked and ignored. Binary cross-entropy can be calculated for both the true outputs and the predicted outputs. The cross-entropy values can be average for each of the indexes in the output and then the cross-entropy values for the 1 and 0 values. Only the indexes that exist in the true output are considered in the loss.

```
def binary_loss ( y_true , y_pred ):
    mask_true = K. c a s t (K. n o t eq u al ( y_true , mask_value ) ,
K. f l o a t x ( ) )
    y_pred = mask_true * y_pred
    y_true = mask_true * y_true
    loc_0 = mask_true *K. c a s t (K. equal ( y_true , 0 ), K. f l o a t x ( )
)
    loc_0_ve_c = K.sum( loc_0 , a x i s = 0 )
    loc_1_ve_c = K.sum(y_true , a x i s = 0 )
    b _ce = K. b i n a r y _crossentropy ( y_true , y_pred )
    loss_0 = K.sum( loc_0 * b_ce , a x i s = 0 )/( loc_0_ve_c +
K. e p s i l o n ( ) )
    loss_1 = K.sum( y_true * b_ce , a x i s = 0 )/( loc_1_ve_c +
K. e p s i l o n ( ) )
    loss_0 = K. mean( tf .boolean_mask ( loss_0 ,
t f. g r e a t e r ( loc_0_ve_c , 0 ) ) )
    loss_1 = K. mean( t f .boolean_mask ( loss_1 ,
t f. g r e a t e r ( loc_1_ve_c , 0 ) ) )
    loss_0 = t f. cond ( t f. math . is_nan ( loss_0 ), lambda :0. 0 ,
lambda : loss_0 )
    loss_1 = t f. cond ( t f. math . is_nan ( loss_1 ), lambda :0. 0 ,
lambda : loss_1 )
    bottom = K. c l i p (K.sum( loc_0_ve_c ) , 0 . 0 ,1 . 0 ) + ¥
    K. c l i p (K.sum( loc_1_ve_c ), 0.0 , 1 . 0 ) + K. e p s i l o n ( )
    loss = (loss_1 + loss_0 )/ bottom
    return loss
```

The loss function below is used by HEARTio for explicit semi-supervised learning. The concatenated feature vector is used to create a reference similarity matrix. Each output of HEARTio is then used to create a comparative similarity matrix. Signals that are similar across the feature vector space should be similar across the output space as well. Binary cross entropy is done between the reference similarity matrix and each output comparative matrix and then averaged.

```
def get_mat ( feature):
    r = tf.reduce_sum(feature*feature, 1)
    r = tf .reshape(r, [− 1, 1])
    D = −1*(r − 2*tf .matmul(feature, feature , transpose _b=True) \
    + tf.transpose(r))
    return (D − K.min(D) + 1 e−7) /(K.max(D) − K.min(D) + 1 e−7)
```

```
def calculate_SSL_loss (reLmat, outpuLlist):
    num_outputs = len (output_list)
    A = get_mat ( ref_mat)
    loss = 0.0
    for output in output_list:
        inter_mat = get_mat(output)
        loss += 1.0/ num_outputs*\
        K. mean(K. binary_crossentropy (A, inter_mat))
    return loss
def SSL_wrapper(ref_mat , output_list):
    return K.in_train_phase (calculate_SSL_loss (ref_mat, output_list) ,0.0)
```

FIG. 9 is a block diagram 2400 of a HEARTio computer device, such as the computer device 104 (FIG. 1), according to various aspects of the present invention. The illustrated computer device 2400 includes multiple processor units 2402A-B that each includes, in the illustrated aspect, multiple (N) sets of processor cores 2404A-N. Each processor unit 2402A-B may include onboard memory (ROM or RAM) (not shown) and off-board memory 2406A-B. The onboard memory may include primary, volatile, and/or non-volatile storage (e.g., storage directly accessible by the processor cores 2404A-N). The off-board memory 2406A-B may include secondary, non-volatile storage (e.g., storage that is not directly accessible by the processor cores 2404A-N), such as ROM, HDDs, SSD, flash, etc. The processor cores 2404A-N may be CPU cores, GPU cores and/or AI accelerator cores. GPU cores operate in parallel (e.g., a general-purpose GPU (GPGPU) pipeline) and, hence, can typically process data more efficiently that a collection of CPU cores, but all the cores of a GPU execute the same code at one time. AI accelerators are a class of microprocessor designed to accelerate artificial neural networks. They typically are employed as a coprocessor in a device with a host processor 2410 as well. An AI accelerator typically has tens of thousands of matrix multiplier units that operate at lower precision than a CPU core, such as 8-bit precision in an AI accelerator versus 64-bit precision in a CPU core.

In various aspects, the different processor cores 2404 may train and/or implement different components of the HEARTio neural model. For example, in one aspect, the cores of the first processor unit 2402A may implement the autoencoder, and the second processor unit 2402B may implement the dense network. In other aspects, one or more of the processor cores 2404 and/or one or more of the processor units could implement other components in the HEARTio neural model. One or more host processors 2410 may coordinate and control the processor units 2402A-B.

In other aspects, the system 2400 could be implemented with one processor unit 2402. In aspects where there are multiple processor units, the processor units could be co-located or distributed. For example, the processor units 2402 may be interconnected by data networks, such as a LAN, WAN, the Internet, etc., using suitable wired and/or wireless data communication links. Data may be shared between the various processing units 2402 using suitable data links, such as data buses (preferably high-speed data buses) or network links (e.g., Ethernet).

The software for the HEARTio model network and other computer functions described herein may be implemented in computer software using any suitable computer programming language, such as .NET, C, C++, or Python, and using conventional, functional, or object-oriented techniques. For example, the HEARTio neural mode may be implemented with software modules stored or otherwise maintained in computer readable media, e.g., RAM, ROM, secondary storage, etc. One or more processing cores (e.g., CPU or GPU cores) of the machine learning system may then execute the software modules to implement the function of the respective machine learning system (e.g., student, coach, etc.). Programming languages for computer software and other computer-implemented instructions may be translated into machine language by a compiler or an assembler before execution and/or may be translated directly at run time by an interpreter. Examples of assembly languages include ARM, MIPS, and x86; examples of high-level languages include Ada, BASIC, C, C++, C#, COBOL, Fortran, Java, Lisp, Pascal, Object Pascal, Haskell, ML; and examples of scripting languages include Bourne script, JavaScript, Python, Ruby, Lua, PHP, and Perl.

The examples presented herein are intended to illustrate potential and specific implementations of the present invention. It can be appreciated that the examples are intended primarily for purposes of illustration of the invention for those skilled in the art. No particular aspect or aspects of the examples are necessarily intended to limit the scope of the present invention. Further, it is to be understood that the figures and descriptions of the present invention have been simplified to illustrate elements that are relevant for a clear understanding of the present invention, while eliminating, for purposes of clarity, other elements. While various aspects have been described herein, it should be apparent that various modifications, alterations, and adaptations to those aspects may occur to persons skilled in the art with attainment of at least some of the advantages. The disclosed aspects are therefore intended to include all such modifications, alterations, and adaptations without departing from the scope of the aspects as set forth herein.

As previously discussed, deep learning, and machine learning models are employed by the HEARTio computer device disclosed herein to classify input biosignals such as electrocardiograms (ECGs) and electroencephalograms (EEGs), for example. Such biosignals can use signal-based methods such as recurrent neural networks, or long-term short-term memory models. HEARTio converts the biosignals into a multi-dimensional input matrix or "biosignal image" of the biosignal. HEARTio then processes the multi-dimensional input matrix/image to classify the initial biosignals.

HEARTio is a multi-output model that has a single input, none of which are demographic or biometric based. HEARTio employs an autoencoder step that can "correct" or "fill-in" any incoming biosignal. This means if there is significant noise or artifact intrinsic in the input biosignal, or if any leads or parts of leads are missing, HEARTio can reconstruct a viable image, such as a 12 lead ECG system, for example. HEARTio can accomplish this with incomplete signal inputs. For example, HEARTio can reconstruct a 12 lead ECG even if there is only 1 viable input lead. Raw Outputs given by the HEARTio deep learning model include and LAD FFR, "70%" Disease threshold, Hypertrophy, Morphology, MI location, ST-T changes, and Conduction disorders.

Training methodologies employed by the HEARTio deep learning model can include different ways of augmenting existing datasets. For example, stripping random segments/leads from the biosignal before inputting the biosignal during the forward pass segment of backpropagation. HEARTio can alter the biosignal, such as by increasing/decreasing the heart rate before input. Alternately and/or additionally, HEARTio can alter a sensor configuration, such as by flipping the leads before input, or reorganizing the leads before input.

Adaptive weight losses changed after every epoch based on the change in performance and loss magnitudes. Training involves organizing each biosignal into a specific "folder" that is associated with a specific output. During training, HEARTio will be inputted with various "folders" such that at the end of a "cycle", each folder has been shown to HEARTio so there is no gap in training. (i.e. a rare output that is only seen 1× every 500 epochs or something). During training, any ECGs that represent a "missing signal" with no useable information are dropped based on a frequency domain analysis. During training, any leads that represent a "missing signal" with no useable information are zero-ed out based on a frequency domain analysis Losses employed by the HEARTio deep learning model during training and evaluation. HEARTio has 4 major classes of custom-made loss functions that are continually weighed for each update. Loss functions include, for example, a weighed binary cross entropy, a weighed categorical cross entropy, a weighed log cosh, and a binned mean log squared error.

Alternatively and/or additionally, HEARTio uses multiple semi-supervised loss functions in order to learn from data where there might not be a clinical output, just the ECG signal itself. For example, HEARTio can use a multi-task learning loss (MTL) that mandates that there is a correlation (either positive or negative) between the latent space and every one of the outputs. In other aspects, HEARTio can use a semi-supervised information loss (SSIL) that tries to have the model find an equilibrium between the information provided by each of the outputs. According to some non-limiting aspects, the semi-supervised loss and MTL losses can be added into an overall loss with some weighting. While the other losses (e.g., adaptive weight losses) can be used to train the model to make correct predictions on the training data, the semi-supervised, amd MTL can make sure that the model is generalized and not overfitting to the training data.

As illustrated in FIGS. 5A-B and 6A-B, HEARTio can provide various visualizations employed by the platform. HEARTio can be device agnostic and configured to utilize any digital biosignal file coming from a biosignal device. If the only available file type is an image or pdf, a rudimentary computer vision algorithm can be used to convert this data type into a digital format. As such, HEARTio can use a full, 12-lead, ECG device or and single lead devices, including a wearable device, such as a smart watch.

According to some non-limiting aspects, the present disclosure contemplates a diagnostic tool, wherein the diagnostic tool includes: a sensor for capturing at least one biosignal produced by a patient's heart; and a computer device that implements a deep neural network that is trained iteratively through machine learning to generate a prediction about a heart condition of the patient, wherein, after the deep neural network is trained, the computer device is configured to: convert the at least one biosignal to a multi-dimensional input matrix for the deep neural network generated from a number (N) of biosignals captured by the sensor, wherein each of the N biosignals is at least "T" seconds, and wherein N is greater than 1; and process the multi-dimensional input matrix through the deep neural network, wherein an output of the deep neural network from processing the multi-dimensional input matrix through the deep neural network corresponds to the prediction about the heart condition of the patient.

In some non-limiting aspects, the deep neural network is a DenseNet including a plurality of layers configured to receive inputs from preceding layers of the plurality and generate outputs for proceeding layers of the plurality, such that each layer of the plurality has a collective knowledge from all preceding layers of the plurality.

In some non-limiting aspects, the biosignal is an ECG signal, and wherein N is 12.

In some non-limiting aspects, the biosignal is an ECG signal, wherein N is less than 12, and wherein the computer device further implements an autoencoder trained via machine learning to generate 12-N biosignals based, at least in part, on a reconstruction loss function.

In some non-limiting aspects, the reconstruction loss function calculates a squared difference between a fast Fourier transform (FFT) between an input of the sensor and an output of the autoencoder.

In some non-limiting aspects, the autoencoder includes: an encoder configured to perform a lossy compression of the at least one biosignal captured by the sensor, wherein an output of the lossy compression is a latent space representation; and a decoder configured to receive the latent space representation from the encoder and convert the latent space representation into a tensorform signal input to the DenseNet.

In some non-limiting aspects, the DenseNet is configured to generate a feature vector based, at least in part, on the tensorform signal.

In some non-limiting aspects, the DenseNet includes: a concatenation layer configured to concatenate the feature vector and the latent space representation into a concatenated feature vector; and a classifier clayer configured to generate outputs based, at least in part, on the concatenated feature vector, and wherein the prediction is generated based, at least in part, on the outputs of the classifier.

In some non-limiting aspects, the output includes at least one of a beat classifications, a rhythm classification, and a coronary condition, or combinations thereof.

In some non-limiting aspects, the coronary condition includes at least one of: a Myocardial Infarction (MI), a risk of a Major Adverse Cardiovascular Event (MACE), a coronary artery disease (CAD), a left anterior descending (LAD) coronary artery fractional flow reserve (FFR), an atherosclerotic cardiovascular disease (ACVD), cardiac hypertrophy, ventricle morphology, an abnormal ST-T wave, a conduction disorder, and a "70%" disease threshold, or combinations thereof.

In some non-limiting aspects, wherein at least one biosignal is an electroencephalogram (EEG).

In some non-limiting aspects, the sensor is a wearable device.

In some non-limiting aspects, T is greater than or equal to 5 second and less than or equal to 15 seconds.

In some non-limiting aspects, the diagnostic tool further includes a display coupled to the computer device, wherein the display is configured to visually represent the output of the deep neural network and the prediction about the heart condition of the patient.

According to some non-limiting aspects, the present disclosure contemplates a method including: training, with a computer system, iteratively through machine learning, a deep neural network to make a prediction about a heart condition of a patient; and after training the deep neural network: capturing, with a sensor, at least one biosignal produced by a patient's heart; converting, by the computer system, the at least one biosignal to an input matrix for the deep neural network, wherein the input matrix includes a multi-dimensional matrix generated from a number (N) of biosignals of at least "T" seconds, where N is greater than 1; and processing, by the computer system, the multi-dimensional input matrix through the deep neural network, wherein an output of the deep neural network from processing the multi-dimensional input matrix through the deep neural network corresponds to the prediction about the heart condition of the patient.

In some non-limiting aspects, the method further includes randomly removing at least one of the N biosignals from the multi-dimensional input matrix prior to processing the multi-dimensional input matrix through the deep neural network.

In some non-limiting aspects, the method further includes altering either the biosignal captured by the sensor or a sensor configuration prior to processing the multi-dimensional input matrix through the deep neural network.

In some non-limiting aspects, the processing is iterative, wherein the deep neural network includes a loss algorithm, and the method further includes: assessing, via the loss algorithm, a weight loss associated with each of the N biosignals in the multi-dimensional input matrix based, at least in part, on a change in performance and/or a loss magnitude; and changing the weight associated with each of the N biosignals for subsequent iterations based, at least in part, on the assessment.

In some non-limiting aspects, the loss function is selected from a group consisting of a weighted binary cross entropy, a weighted categorical cross entropy, a weighted log cosh, and a binned mean log squared error.

In some non-limiting aspects, the loss function is semi-supervised and is either a multi-task learning loss (MTL) configured to correlate latent space and a each of a plurality of outputs or a semi-supervised information loss (SSIL) configured to find an equilibrium between information provided by each the output and a plurality of possible outputs.

In some non-limiting aspects, the method further includes organizing the sensor into one of a plurality of folders, wherein each of the plurality of folders is associated with at least one of the plurality of possible outputs.

In some non-limiting aspects, the method further includes: assigning, by the computer system, a corresponding label to each of the plurality of outputs; determining, by the computer system, that at least one output of the plurality of outputs does not have a corresponding label; and creating, by the computer system, a label corresponding to the at least one output of the plurality of outputs.

According to some non-limiting aspects, the present disclosure contemplates a computer system including one or more processor cores, wherein the one or more processor cores are configured to: train, iteratively through machine learning, a deep neural network to make a prediction about a heart condition of a patient; and after training the deep neural network: receive, from a sensor, at least one ECG signal produced by a patient's heart and captured by the sensor; convert the at least one ECG signal to an input matrix for the deep neural network, wherein the input matrix includes a multi-dimensional [or multi-axis] matrix generated from N ECG signals of at least T seconds, where N is greater than 1; and process the input matrix through the deep neural network, wherein an output of the deep neural network from processing the input matrix through the deep neural network corresponds to the prediction about the heart condition of the patient.

The examples presented herein are intended to illustrate potential and specific implementations of the present invention. It can be appreciated that the examples are intended primarily for purposes of illustration of the invention for those skilled in the art. No particular aspect or aspects of the examples are necessarily intended to limit the scope of the present invention. Further, it is to be understood that the figures and descriptions of the present invention have been simplified to illustrate elements that are relevant for a clear understanding of the present invention, while eliminating, for purposes of clarity, other elements. While various aspects have been described herein, it should be apparent that various modifications, alterations, and adaptations to those aspects may occur to persons skilled in the art with attainment of at least some of the advantages. For example, functions explicitly described as performed by the previously disclosed diagnostic tool can be claimed as a method independent of the diagnostic tool, itself. Likewise, it shall be appreciated that the previously disclosed diagnostic tool can be further configured and claimed to perform steps explicitly described in reference to the methods disclosed herein. As such, the disclosed embodiments are therefore intended to include all such modifications, alterations, and adaptations without departing from the scope of the aspects as set forth herein.

APPENDIX A

TABLE 4

| Category & Sub-indexes |
| --- |
| Blockage |

LAD %
LCX %
RCA %
LM %

| MI & History |
| --- |

Acute MI
Prior MI
NSTEMI
Prior GABG
Prior PCI

| Beats |
| --- |

Ventricular flutter wave
Paced beat
Atrial premature beat
Ventricular escape beat
Fusion of ventricular and normal beat
Nodal (junctional) premature beat
Left bundle branch block beat
Normal beat
Unclassifiable beat
Supraventricular premature or ectopic beat (atrial or nodal)
Right bundle branch block beat
Premature ventricular contraction
Aberrated atrial premature beat
Atrial escape beat
Fusion of paced and normal beat
Nodal (junctional) escape beat
Non-conducted P-wave (blocked APC)

| Rhythm |
| --- |

Atrial bigeminy
Atrial fibrillation
Atrial flutter
Ventricular bigeminy
First heart block
Second heart block
Idioventricular rhythm
Normal sinus rhythm
Nodal (A-V junctional) rhythm
Paced rhythm
Pre-excitation (WPW)
Sinus bradycardia
Supraventricular tachyarrhythmia
Ventricular trigeminy
Ventricular flutter
Ventricular tachycardia
Noise

TABLE 4-continued

| Category & Sub-indexes |
| --- |
| MACE |
| None |
| MI |
| Stroke |
| Syncope |
| Label-Overall |
| Low-Mild |
| Moderate |
| Severe |
| Binary Blockage |
| LAD |
| RCA |
| LCX |
| LM |
| Bloodtests |
| Troponin Initial |
| Troponin Peak |
| CK peak |
| CKMB peak |
| Complications |
| Cardiac Arrest |
| Cardiogenic Shock |
| Severe Heart Failure - Pulmonary Edema |
| Extension of MI |
| Ejection Fraction |
| Ejection Fraction % |
| Disease |
| Significant Disease |
| SPECT |
| Segment 0 |
| Segment 1 |
| Segment 2 |
| Segment 3 |
| Segment 4 |
| Segment 5 |
| Segment 6 |
| Segment 7 |
| Segment 8 |
| Segment 9 |
| Segment 10 |
| Segment 11 |
| Segment 12 |
| Segment 13 |
| Segment 14 |
| Segment 15 |
| Segment 16 |
| Segment 17 |
| Segment 18 |
| Segment 19 |
| Conduction Disorders |
| Left Anterior Fascicular Block |
| Incomplete Right Bundle Branch Block |
| First Degree AV Block |
| Non-specific Intraventricular Conduction Disturbance (Block) |
| Complete Right Bundle Branch Block |
| Complete Left Bundle Branch Block |
| Left Posterior Fascicular Block |
| Wolf-Parkinson-White syndrome |
| Incomplete Left Bundle Branch Block |
| Third Degree AV Block |
| Second Degree AV Block |
| Hypertrophy |
| Left Ventricular Hypertrophy |
| Left Atrial Overload/Enlargement |
| Right Ventricular Hypertrophy |
| Right Atrial Overload/Enlargement |
| Septal Hypertrophy |
| Location of MI |
| inferior myocardial infarction |
| anteroseptal myocardial infarction |
| inferolateral myocardial infarction |
| anterior myocardial infarction |
| anterolateral myocardial infarction |
| subendocardial injury in anteroseptal leads |
| lateral myocardial infarction |
| subendocardial injury in anterolateral leads |
| inferoposterolateral myocardial infarction |
| inferoposterior myocardial infarction |
| subendocardial injury in inferior leads |
| subendocardial injury in lateral leads |
| posterior myocardial infarction |
| subendocardial injury in inferolateral leads |
| Morphology |
| abnormal QRS |
| ventricular premature complex |
| non-specific ST depression |
| voltage criteria (QRS) for left ventricular hypertrophy |
| Q waves present |
| low amplitude T-waves |
| non-specific T-wave changes |
| atrial premature complex |
| prolonged PR interval |
| inverted T-waves |
| low QRS voltages in the frontal and horizontal leads |
| high QRS voltage |
| T-wave abnormality |
| non-specific ST elevation |
| premature complex(es) |
| ST-T Changes |
| non-diagnostic T abnormalities |
| non-specific ST changes |
| digitalis-effect |
| long QT-interval |
| non-specific ischemic |
| ischemic in anterolateral leads |
| ischemic in inferior leads |
| ischemic in inferolateral leads |
| ischemic in anteroseptal leads |
| ischemic in lateral leads |
| ST-T changes compatible with ventricular aneurysm |
| electrolytic disturbance or drug (former EDIS) |
| ischemic in anterior leads |
| Ejection Fraction Binary |
| Ejection Fraction Binary |
| FFR |
| LAD FFR % |
| FFR Binary |
| LAD FFR Binary |
| 70% Disease |
| Significant Disease |

APPENDIX B

TABLE 5

| Model: "Encoder" | | |
| --- | --- | --- |
| Layer (type) | Output Shape | Param # |
| input 1 (InputLayer) | (None, 1000, 12, 1) | 0 |
| gaussian dropout 1 (Gaussian | (None, 1000, 12, 1) | 0 |
| zero padding2d 1 (ZeroPaddin | (None, 1004, 12, 1) | 0 |
| conv2d 1 (Conv2D) | (None, 500, 12, 32) | 160 |
| leaky re lu 1 (LeakyReLU) | (None, 500, 12, 32) | 0 |

TABLE 5-continued

Model: "Encoder"

| Layer (type) | Output Shape | Param # |
|---|---|---|
| batch normalization 1 (Batch | (None, 500, 12, 32) | 128 |
| zero padding2d 2 (ZeroPaddin | (None, 504, 12, 32) | 0 |
| conv2d 2 (Conv2D) | (None, 250, 12, 64) | 10240 |
| leaky re lu 2 (LeakyReLU) | (None, 250, 12, 64) | 0 |
| batch normalization 2 (Batch | (None, 250, 12, 64) | 256 |
| zero padding2d 3 (ZeroPaddin | (None, 254, 12, 64) | 0 |
| conv2d 3 (Conv2D) | (None, 125, 12, 96) | 30720 |
| leaky re lu 3 (LeakyReLU) | (None, 125, 12, 96) | 0 |
| batch normalization 3 (Batch | (None, 125, 12, 96) | 384 |
| zero padding2d 4 (ZeroPaddin | (None, 129, 12, 96) | 0 |
| conv2d 4 (Conv2D) | (None, 63, 12, 128) | 61440 |
| leaky re lu 4 (LeakyReLU) | (None, 63, 12, 128) | 0 |
| batch normalization 4 (Batch | (None, 63, 12, 128) | 512 |
| zero padding2d 5 (ZeroPaddin | (None, 67, 12, 128) | 0 |
| conv2d 5 (Conv2D) | (None, 32, 12, 160) | 102400 |
| leaky re lu 5 (LeakyReLU) | (None, 32, 12, 160) | 0 |
| batch normalization 5 (Batch | (None, 32, 12, 160) | 640 |
| zero padding2d 6 (ZeroPaddin | (None, 36, 12, 160) | 0 |
| conv2d 6 (Conv2D) | (None, 16, 12, 192) | 153600 |
| leaky re lu 6 (LeakyReLU) | (None, 16, 12, 192) | 0 |
| batch normalization 6 (Batch | (None, 16, 12, 192) | 768 |
| zero padding2d 7 (ZeroPaddin | (None, 20, 12, 192) | 0 |
| conv2d 7 (Conv2D) | (None, 8, 12, 224) | 215040 |
| leaky re lu 7 (LeakyReLU) | (None, 8, 12, 224) | 0 |
| batch normalization 7 (Batch | (None, 8, 12, 224) | 896 |
| zero padding2d 8 (ZeroPaddin | (None, 12, 12, 224) | 0 |
| conv2d 8 (Conv2D) | (None, 4, 12, 256) | 286720 |
| leaky re lu 8 (LeakyReLU) | (None, 4, 12, 256) | 0 |
| batch normalization 8 (Batch | (None, 4, 12, 256) | 1024 |
| flatten 1 (Flatten) | (None, 12288) | 0 |
| dense 1 (Dense) | (None, 1024) | 12582912 |
| leaky re lu 9 (LeakyReLU) | (None, 1024) | 0 |
| batch normalization 9 (Batch | (None, 1024) | 4096 |

Total params: 13,451,936
Trainable params: 13,447,584
Non-trainable params: 4,352

APPENDIX C

TABLE 6

Model: "Decoder"

| Layer (type) | Output Shape | Param # |
|---|---|---|
| input 2 (InputLayer) | (None, 1024) | 0 |
| dense 2 (Dense) | (None, 12288) | 12582912 |
| leaky re lu 10 (LeakyReLU) | (None, 12288) | 0 |
| batch normalization 10 (Bate | (None, 12288) | 49152 |
| reshape 1 (Reshape) | (None, 4, 12, 256) | 0 |
| conv2d transpose 1 (Conv2DTr | (None, 10, 12, 224) | 229600 |
| leaky re lu 11 (LeakyReLU) | (None, 10, 12, 224) | 0 |
| cropping2d 1 (Cropping2D) | (None, 8, 12, 224) | 0 |
| batch normalization 11 (Bate | (None, 8, 12, 224) | 896 |
| conv2d transpose 2 (Conv2DTr | (None, 18, 12, 192) | 172224 |
| leaky re lu 12 (LeakyReLU) | (None, 18, 12, 192) | 0 |
| cropping2d 2 (Cropping2D) | (None, 16, 12, 192) | 0 |
| batch normalization 12 (Bate | (None, 16, 12, 192) | 768 |
| conv2d transpose 3 (Conv2DTr | (None, 34, 12, 160) | 123040 |
| leaky re lu 13 (LeakyReLU) | (None, 34, 12, 160) | 0 |
| cropping2d 3 (Cropping2D) | (None, 32, 12, 160) | 0 |
| batch normalization 13 (Bate | (None, 32, 12, 160) | 640 |
| conv2d transpose 4 (Conv2DTr | (None, 66, 12, 128) | 82048 |
| leaky re lu 14 (LeakyReLU) | (None, 66, 12, 128) | 0 |
| cropping2d 4 (Cropping2D) | (None, 64, 12, 128) | 0 |
| batch normalization 14 (Bate | (None, 64, 12, 128) | 512 |
| conv2d transpose 5 (Conv2DTr | (None, 130, 12, 96) | 49248 |
| leaky re lu 15 (LeakyReLU) | (None, 130, 12, 96) | 0 |
| cropping2d 5 (Cropping2D) | (None, 128, 12, 96) | 0 |
| batch normalization 15 (Bate | (None, 128, 12, 96) | 384 |
| conv2d transpose 6 (Conv2DTr | (None, 258, 12, 64) | 24640 |
| leaky re lu 16 (LeakyReLU) | (None, 258, 12, 64) | 0 |
| cropping2d 6 (Cropping2D) | (None, 256, 12, 64) | 0 |
| batch normalization 16 (Bate | (None, 256, 12, 64) | 256 |
| conv2d transpose 7 (Conv2DTr | (None, 514, 12, 32) | 8224 |
| leaky re lu 17 (LeakyReLU) | (None, 514, 12, 32) | 0 |
| cropping2d 7 (Cropping2D) | (None, 512, 12, 32) | 0 |
| batch normalization 17 (Bate | (None, 512, 12, 32) | 128 |
| conv2d transpose 8 (Conv2DTr | (None, 1026, 12, 1) | 129 |
| cropping2d 8 (Cropping2D) | (None, 1000, 12, 1) | 0 |

Total params: 13,324,801
Trainable params: 13,298,433

APPENDIX D

TABLE 8

Model: "Densenet"

| Layer (type) | Output Shape | Param # | Connected to |
|---|---|---|---|
| input 1 (InputLayer) | (None, 1000, 12, 1) | 0 | |
| zero padding2d 1 (ZeroPadding2D | (None, 1006, 12, 1) | 0 | input 1[0][0] |
| conv1/conv (Conv2D) | (None, 500, 12, 64) | 448 | zero padding2d 1[0][0] |
| conv1/bn (BatchNormalization) | (None, 500, 12, 64) | 256 | conv1/conv[0][0] |
| conv1/relu (Activation) | (None, 500, 12, 64) | 0 | conv1/bn [0][0] |
| zero padding2d 2 (ZeroPadding2D | (None, 502, 12, 64) | 0 | conv1/relu[0][0] |
| pool1 (MaxPooling2D) | (None, 250, 12, 64) | 0 | zero padding2d 2[0][0] |
| conv2 block1 0 bn (BatchNormali | (None, 250, 12, 64) | 256 | pool1[0][0] |
| conv2 block1 0 relu (Activation | (None, 250, 12, 64) | 0 | conv2 block1 0 bn[0][0] |
| conv2 block1 1 conv (Conv2D) | (None, 250, 12, 128) | 8192 | conv2 block1 0 relu[0][0] |
| conv2 block1 1 bn (BatchNormali | (None, 250, 12, 128) | 512 | conv2 block1 1 conv[0][0] |
| conv2 block1 1 relu (Activation | (None, 250, 12, 128) | 0 | conv2 block1 1 bn[0][0] |
| conv2 block1 2 conv (Conv2D) | (None, 250, 12, 32) | 12288 | conv2 block1 1 relu[0][0] |
| conv2 block1 concat (Concatenat | (None, 250, 12, 96) | 0 | pool1[0][0]<br>conv2 block1 2 conv[0][0] |
| conv2 block2 0 bn (BatchNormali | (None, 250, 12, 96) | 384 | conv2 block1 concat[0][0] |
| conv2 block2 0 relu (Activation | (None, 250, 12, 96) | 0 | conv2 block2 0 bn[0][0] |
| conv2 block2 1 conv (Conv2D) | (None, 250, 12, 128) | 12288 | conv2 block2 0 relu[0][0] |
| conv2 block2 1 bn (BatchNormali | (None, 250, 12, 128) | 512 | conv2 block2 1 conv[0][0] |
| conv2 block2 1 relu (Activation | (None, 250, 12, 128) | 0 | conv2 block2 1 bn[0][0] |
| conv2 block2 2 conv (Conv2D) | (None, 250, 12, 32) | 12288 | conv2 block2 1 relu[0][0] |
| conv2 block2 concat (Concatenat | (None, 250, 12, 128) | 0 | conv2 block1 concat[0][0]<br>conv2 block2 2 conv[0][0] |

TABLE 8-continued

Model: "Densenet"

| Layer (type) | Output Shape | Param # | Connected to |
|---|---|---|---|
| conv2 block3 0 bn (BatchNormali | (None, 250, 12, 128) | 512 | conv2 block2 concat[0][0] |
| conv2 block3 0 relu (Activation | (None, 250, 12, 128) | 0 | conv2 block3 0 bn[0][0] |
| conv2 block3 1 conv (Conv2D) | (None, 250, 12, 128) | 16384 | conv2 block3 0 relu[0][0] |
| conv2 block3 1 bn (BatchNormali | (None, 250, 12, 128) | 512 | conv2 block3 1 conv[0][0] |
| conv2 block3 1 relu (Activation | (None, 250, 12, 128) | 0 | conv2 block2 1 bn[0][0] |
| conv2 block3 2 conv (Conv2D) | (None, 250, 12, 32) | 12288 | conv2 block3 1 relu[0][0] |
| conv2 block3 concat (Concatenat | (None, 250, 12, 160) | 0 | conv2 block2 concat[0][0] |
| | | | conv2 block3 2 conv[0][0] |
| conv2 block4 0 bn (BatchNormali | (None, 250, 12, 160) | 640 | conv2 block3 concat[0][0] |
| conv2 block4 0 relu (Activation | (None, 250, 12, 160) | 0 | conv2 block4 0 bn[0][0] |
| conv2 block4 1 conv (Conv2D) | (None, 250, 12, 128) | 20480 | conv2 block4 0 relu[0][0] |
| conv2 block4 1 bn (BatchNormali | (None, 250, 12, 128) | 512 | conv2 block4 1 conv[0][0] |
| conv2 block4 1 relu (Activation | (None, 250, 12, 128) | 0 | conv2 block4 1 bn[0][0] |
| conv2 block4 2 conv (Conv2D) | (None, 250, 12, 32) | 12288 | conv2 block4 1 relu[0][0] |
| conv2 block4 concat (Concatenat | (None, 250, 12, 192) | 0 | conv2 block3 concat[0][0] |
| | | | conv2 block4 2 conv[0][0] |
| conv2 block5 0 bn (BatchNormali | (None, 250, 12, 192) | 768 | conv2 block4 concat[0][0] |
| conv2 block5 0 relu (Activation | (None, 250, 12, 192) | 0 | conv2 block5 0 bn[0][0] |
| conv2 block5 1 conv (Conv2D) | (None, 250, 12, 128) | 24576 | conv2 block5 0 relu[0][0] |
| conv2 block5 1 bn (BatchNormali | (None, 250, 12, 128) | 512 | conv2 block5 1 conv[0][0] |
| conv2 block5 1 relu (Activation | (None, 250, 12, 128) | 0 | conv2 block5 1 bn[0][0] |
| conv2 block5 2 conv (Conv2D) | (None, 250, 12, 32) | 12288 | conv2 block5 1 relu[0][0] |
| conv2 block5 concat (Concatenat | (None, 250, 12, 224) | 0 | conv2 block4 concat[0][0] |
| | | | conv2 block5 2 conv[0][0] |
| conv2 block6 0 bn (BatchNormali | (None, 250, 12, 224) | 896 | conv2 block5 concat[0][0] |
| conv2 block6 0 relu (Activation | (None, 250, 12, 224) | 0 | conv2 block6 0 bn[0][0] |
| conv2 block6 1 conv (Conv2D) | (None, 250, 12, 128) | 28672 | conv2 block6 0 relu[0][0] |
| conv2 block6 1 bn (BatchNormali | (None, 250, 12, 128) | 512 | conv2 block6 1 conv[0][0] |
| conv2 block6 1 relu (Activation | (None, 250, 12, 128) | 0 | conv2 block6 1 bn[0][0] |
| conv2 block6 2 conv (Conv2D) | (None, 250, 12, 32) | 12288 | conv2 block6 1 relu[0][0] |
| conv2 block6 concat (Concatenat | (None, 250, 12, 256) | 0 | conv2 block5 concat[0][0] |
| | | | conv2 block6 2 conv[0][0] |
| pool2 bn (BatchNormalization) | (None, 250, 12, 256) | 1024 | conv2 block6 concat[0][0] |
| pool2 relu (Activation) | (None, 250, 12, 256) | 0 | pool2 bn[0][0] |
| pool2 conv (Conv2D) | (None, 250, 12, 128) | 32768 | pool2 relu[0][0] |
| pool2 pool (AveragePooling2D) | (None, 125, 12, 128) | 0 | pool2 conv[0][0] |
| conv3 block1 0 bn (BatchNormali | (None, 125, 12, 128) | 512 | pool2 pool[0][0] |
| conv3 block1 0 relu (Activation | (None, 125, 12, 128) | 0 | conv3 block1 0 bn[0][0] |
| conv3 block1 1 conv (Conv2D) | (None, 125, 12, 128) | 16384 | conv3 block1 0 relu[0][0] |
| conv3 block1 1 bn (BatchNormali | (None, 125, 12, 128) | 512 | conv3 block1 1 conv[0][0] |
| conv3 block1 1 relu (Activation | (None, 125, 12, 128) | 0 | conv3 block1 1 bn[0][0] |
| conv3 block1 2 conv (Conv2D) | (None, 125, 12, 32) | 12288 | conv3 block1 1 relu[0][0] |
| conv3 block1 concat (Concatenat | (None, 125, 12, 160) | 0 | pool2 pool[0][0] |
| | | | conv3 block1 2 conv[0][0] |
| conv3 block2 0 bn (BatchNormali | (None, 125, 12, 160) | 640 | conv3 block1 concat[0][0] |
| conv3 block2 0 relu (Activation | (None, 125, 12, 160) | 0 | conv3 block2 0 bn[0][0] |
| conv3 block2 1 conv (Conv2D) | (None, 125, 12, 128) | 20480 | conv3 block2 0 relu[0][0] |
| conv3 block2 1 bn (BatchNormali | (None, 125, 12, 128) | 512 | conv3 block2 1 conv[0][0] |
| conv3 block2 1 relu (Activation | (None, 125, 12, 128) | 0 | conv3 block2 1 bn[0][0] |
| conv3 block2 2 conv (Conv2D) | (None, 125, 12, 32) | 12288 | conv3 block2 1 relu[0][0] |
| conv3 block2 concat (Concatenat | (None, 125, 12, 192) | 0 | conv3 block1 concat[0][0] |
| | | | conv3 block2 2 conv[0][0] |
| conv3 block3 0 bn (BatchNormali | (None, 125, 12, 192) | 768 | conv3 block2 concat[0][0] |
| conv3 block3 0 relu (Activation | (None, 125, 12, 192) | 0 | conv3 block3 0 bn[0][0] |
| conv3 block3 1 conv (Conv2D) | (None, 125, 12, 128) | 24576 | conv3 block3 0 relu[0][0] |
| conv3 block3 1 bn (BatchNormali | (None, 125, 12, 128) | 512 | conv3 block3 1 conv[0][0] |
| conv3 block3 1 relu (Activation | (None, 125, 12, 128) | 0 | conv3 block3 1 bn[0][0] |
| conv3 block3 2 conv (Conv2D) | (None, 125, 12, 32) | 12288 | conv3 block3 1 relu[0][0] |
| conv3 block3 concat (Concatenat | (None, 125, 12, 224) | 0 | conv3 block2 concat[0][0] |
| | | | conv3 block3 2 conv[0][0] |
| conv3 block4 0 bn (BatchNormali | (None, 125, 12, 224) | 896 | conv3 block3 concat[0][0] |
| conv3 block4 0 relu (Activation | (None, 125, 12, 224) | 0 | conv3 block4 0 bn[0][0] |
| conv3 block4 1 conv (Conv2D) | (None, 125, 12, 128) | 28672 | conv3 block4 0 relu[0][0] |
| conv3 block4 1 bn (BatchNormali | (None, 125, 12, 128) | 512 | conv3 block4 1 conv[0][0] |
| conv3 block4 1 relu (Activation | (None, 125, 12, 128) | 0 | conv3 block4 1 bn[0][0] |
| conv3 block4 2 conv (Conv2D) | (None, 125, 12, 32) | 12288 | conv3 block4 1 relu[0][0] |
| conv3 block4 concat (Concatenat | (None, 125, 12, 256) | 0 | conv3 block3 concat[0][0] |
| | | | conv3 block4 2 conv[0][0] |
| conv3 block5 0 bn (BatchNormali | (None, 125, 12, 256) | 1024 | conv3 block4 concat[0][0] |
| conv3 block5 0 relu (Activation | (None, 125, 12, 256) | 0 | conv3 block5 0 bn[0][0] |
| conv3 block5 1 conv (Conv2D) | (None, 125, 12, 128) | 32768 | conv3 block5 0 relu[0][0] |
| conv3 block5 1 bn (BatchNormali | (None, 125, 12, 128) | 512 | conv3 block5 1 conv[0][0] |
| conv3 block5 1 relu (Activation | (None, 125, 12, 128) | 0 | conv3 block5 1 bn[0][0] |
| conv3 block5 2 conv (Conv2D) | (None, 125, 12, 32) | 12288 | conv3 block5 1 relu[0][0] |
| conv3 block5 concat (Concatenat | (None, 125, 12, 288) | 0 | conv3 block4 concat[0][0] |
| | | | conv3 block5 2 conv[0][0] |

TABLE 8-continued

Model: "Densenet"

| Layer (type) | Output Shape | Param # | Connected to |
|---|---|---|---|
| conv3 block6 0 bn (BatchNormali | (None, 125, 12, 288) | 1152 | conv3 block5 concat[0][0] |
| conv3 block6 0 relu (Activation | (None, 125, 12, 288) | 0 | conv3 block6 0 bn[0][0] |
| conv3 block6 1 conv (Conv2D) | (None, 125, 12, 128) | 36864 | conv3 block6 0 relu[0][0] |
| conv3 block6 1 bn (BatchNormali | (None, 125, 12, 128) | 512 | conv3 block6 1 conv[0][0] |
| conv3 block6 1 relu (Activation | (None, 125, 12, 128) | 0 | conv3 block6 1 bn[0][0] |
| conv3 block6 2 conv (Conv2D) | (None, 125, 12, 32) | 12288 | conv3 block6 1 relu[0][0] |
| conv3 block6 concat (Concatenat | (None, 125, 12, 320) | 0 | conv3 block5 concat[0][0] |
|  |  |  | conv3 block6 2 conv[0][0] |
| conv3 block7 0 bn (BatchNormali | (None, 125, 12, 320) | 1280 | conv3 block6 concat[0][0] |
| conv3 block7 0 relu (Activation | (None, 125, 12, 320) | 0 | conv3 block7 0 bn[0][0] |
| conv3 block7 1 conv (Conv2D) | (None, 125, 12, 128) | 40960 | conv3 block7 0 relu[0][0] |
| conv3 block7 1 bn (BatchNormali | (None, 125, 12, 128) | 512 | conv3 block7 1 conv[0][0] |
| conv3 block7 1 relu (Activation | (None, 125, 12, 128) | 0 | conv3 block7 1 bn[0][0] |
| conv3 block7 2 conv (Conv2D) | (None, 125, 12, 32) | 12288 | conv3 block7 1 relu[0][0] |
| conv3 block7 concat (Concatenat | (None, 125, 12, 352) | 0 | conv3 block6 concat[0][0] |
|  |  |  | conv3 block7 2 conv[0][0] |
| conv3 block8 0 bn (BatchNormali | (None, 125, 12, 352) | 1408 | conv3 block7 concat[0][0] |
| conv3 block8 0 relu (Activation | (None, 125, 12, 352) | 0 | conv3 block8 0 bn[0][0] |
| conv3 block8 1 conv (Conv2D) | (None, 125, 12, 128) | 45056 | conv3 block8 0 relu[0][0] |
| conv3 block8 1 bn (BatchNormali | (None, 125, 12, 128) | 512 | conv3 block8 1 conv[0][0] |
| conv3 block8 1 relu (Activation | (None, 125, 12, 128) | 0 | conv3 block8 1 bn[0][0] |
| conv3 block8 2 conv (Conv2D) | (None, 125, 12, 32) | 12288 | conv3 block8 1 relu[0][0] |
| conv3 block8 concat (Concatenat | (None, 125, 12, 384) | 0 | conv3 block7 concat[0][0] |
|  |  |  | conv3 block8 2 conv[0][0] |
| conv3 block9 0 bn (BatchNormali | (None, 125, 12, 384) | 1536 | conv3 block8 concat[0][0] |
| conv3 block9 0 relu (Activation | (None, 125, 12, 384) | 0 | conv3 block9 0 bn[0][0] |
| conv3 block9 1 conv (Conv2D) | (None, 125, 12, 128) | 49152 | conv3 block9 0 relu[0][0] |
| conv3 block9 1 bn (BatchNormali | (None, 125, 12, 128) | 512 | conv3 block9 1 conv[0][0] |
| conv3 block9 1 relu (Activation | (None, 125, 12, 128) | 0 | conv3 block9 1 bn[0][0] |
| conv3 block9 2 conv (Conv2D) | (None, 125, 12, 32) | 12288 | conv3 block9 1 relu[0][0] |
| conv3 block9 concat (Concatenat | (None, 125, 12, 416) | 0 | conv3 block8 concat[0][0] |
|  |  |  | conv3 block9 2 conv[0][0] |
| conv3 block10 0 bn (BatchNormal | (None, 125, 12, 416) | 1664 | conv3 block9 concat[0][0] |
| conv3 block10 0 relu (Activatio | (None, 125, 12, 416) | 0 | conv3 block10 0 bn[0][0] |
| conv3 block10 1 conv (Conv2D) | (None, 125, 12, 128) | 53248 | conv3 block10 0 relu[0][0] |
| conv3 block10 1 bn (BatchNormal | (None, 125, 12, 128) | 512 | conv3 block10 1 conv[0][0] |
| conv3 block10 1 relu (Activatio | (None, 125, 12, 128) | 0 | conv3 block10 1 bn[0][0] |
| conv3 block10 2 conv (Conv2D) | (None, 125, 12, 32) | 12288 | conv3 block10 1 relu[0][0] |
| conv3 block10 concat (Concatena | (None, 125, 12, 448) | 0 | conv3 block9 concat[0][0] |
|  |  |  | conv3 block10 2 conv[0][0] |
| conv3 block11 0 bn (BatchNormal | (None, 125, 12, 448) | 1792 | conv3 block10 concat[0][0] |
| conv3 block11 0 relu (Activatio | (None, 125, 12, 448) | 0 | conv3 block11 0 bn[0][0] |
| conv3 block11 1 conv (Conv2D) | (None, 125, 12, 128) | 57344 | conv3 block11 0 relu[0][0] |
| conv3 block11 1 bn (BatchNormal | (None, 125, 12, 128) | 512 | conv3 block11 1 conv[0][0] |
| conv3 block11 1 relu (Activatio | (None, 125, 12, 128) | 0 | conv3 block11 1 bn[0][0] |
| conv3 block11 2 conv (Conv2D) | (None, 125, 12, 32) | 12288 | conv3 block11 1 relu[0][0] |
| conv3 block11 concat (Concatena | (None, 125, 12, 480) | 0 | conv3 block10 concat[0][0] |
|  |  |  | conv3 block11 2 conv[0][0] |
| conv3 block12 0 bn (BatchNormal | (None, 125, 12, 480) | 1920 | conv3 block11 concat[0][0] |
| conv3 block12 0 relu (Activatio | (None, 125, 12, 480) | 0 | conv3 block12 0 bn[0][0] |
| conv3 block12 1 conv (Conv2D) | (None, 125, 12, 128) | 61440 | conv3 block12 0 relu[0][0] |
| conv3 block12 1 bn (BatchNormal | (None, 125, 12, 128) | 512 | conv3 block12 1 conv[0][0] |
| conv3 block12 1 relu (Activatio | (None, 125, 12, 128) | 0 | conv3 block12 1 bn[0][0] |
| conv3 block12 2 conv (Conv2D) | (None, 125, 12, 32) | 12288 | conv3 block12 1 relu[0][0] |
| conv3 block12 concat (Concatena | (None, 125, 12, 512) | 0 | conv3 block11 concat[0][0] |
|  |  |  | conv3 block12 2 conv[0][0] |
| pool3 bn (BatchNormalization) | (None, 125, 12, 512) | 2048 | conv3 block12 concat[0][0] |
| pool3 relu (Activation) | (None, 125, 12, 512) | 0 | pool3 bn[0][0] |
| pool3 conv (Conv2D) | (None, 125, 12, 256) | 131072 | pool3 relu[0][0] |
| pool3 pool (AveragePooling2D) | (None, 62, 12, 256) | 0 | pool3 conv[0][0] |
| conv4 block1 0 bn (BatchNormali | (None, 62, 12, 256) | 1024 | pool3 pool[0][0] |
| conv4 block1 0 relu (Activation | (None, 62, 12, 256) | 0 | conv4 block1 0 bn[0][0] |
| conv4 block1 1 conv (Conv2D) | (None, 62, 12, 128) | 32768 | conv4 block1 0 relu[0][0] |
| conv4 block1 1 bn (BatchNormali | (None, 62, 12, 128) | 512 | conv4 block1 1 conv[0][0] |
| conv4 block1 1 relu (Activation | (None, 62, 12, 128) | 0 | conv4 block1 1 bn[0][0] |
| conv4 block1 2 conv (Conv2D) | (None, 62, 12, 32) | 12288 | conv4 block1 1 relu[0][0] |
| conv4 block1 concat (Concatenat | (None, 62, 12, 288) | 0 | pool3 pool[0][0] |
|  |  |  | conv4 block1 2 conv[0][0] |
| conv4 block2 0 bn (BatchNormali | (None, 62, 12, 288) | 1152 | conv4 block1 concat[0][0] |
| conv4 block2 0 relu (Activation | (None, 62, 12, 288) | 0 | conv4 block2 0 bn[0][0] |
| conv4 block2 1 conv (Conv2D) | (None, 62, 12, 128) | 36864 | conv4 block2 0 relu[0][0] |
| conv4 block2 1 bn (BatchNormali | (None, 62, 12, 128) | 512 | conv4 block2 1 conv[0][0] |
| conv4 block2 1 relu (Activation | (None, 62, 12, 128) | 0 | conv4 block2 1 bn[0][0] |
| conv4 block2 2 conv (Conv2D) | (None, 62, 12, 32) | 12288 | conv4 block2 1 relu[0][0] |
| conv4 block2 concat (Concatenat | (None, 62, 12, 320) | 0 | conv4 block1 concat[0][0] |
|  |  |  | conv4 block2 2 conv[0][0] |

TABLE 8-continued

Model: "Densenet"

| Layer (type) | Output Shape | Param # | Connected to |
|---|---|---|---|
| conv4 block3 0 bn (BatchNormali | (None, 62, 12, 320) | 1280 | conv4 block2 concat[0][0] |
| conv4 block3 0 relu (Activation | (None, 62, 12, 320) | 0 | conv4 block3 0 bn[0][0] |
| conv4 block3 1 conv (Conv2D) | (None, 62, 12, 128) | 40960 | conv4 block3 0 relu[0][0] |
| conv4 block3 1 bn (BatchNormali | (None, 62, 12, 128) | 512 | conv4 block3 1 conv[0][0] |
| conv4 block3 1 relu (Activation | (None, 62, 12, 128) | 0 | conv4 block3 1 bn[0][0] |
| conv4 block3 2 conv (Conv2D) | (None, 62, 12, 32) | 12288 | conv4 block3 1 relu[0][0] |
| conv4 block3 concat (Concatenat | (None, 62, 12, 352) | 0 | conv4 block2 concat[0][0] |
| | | | conv4 block3 2 conv[0][0] |
| conv4 block4 0 bn (BatchNormali | (None, 62, 12, 352) | 1408 | conv4 block3 concat[0][0] |
| conv4 block4 0 relu (Activation | (None, 62, 12, 352) | 0 | conv4 block4 0 bn[0][0] |
| conv4 block4 1 conv (Conv2D) | (None, 62, 12, 128) | 45056 | conv4 block4 0 relu[0][0] |
| conv4 block4 1 bn (BatchNormali | (None, 62, 12, 128) | 512 | conv4 block4 1 conv[0][0] |
| conv4 block4 1 relu (Activation | (None, 62, 12, 128) | 0 | conv4 block4 1 bn[0][0] |
| conv4 block4 2 conv (Conv2D) | (None, 62, 12, 32) | 12288 | conv4 block4 1 relu[0][0] |
| conv4 block4 concat (Concatenat | (None, 62, 12, 384) | 0 | conv4 block3 concat[0][0] |
| | | | conv4 block4 2 conv[0][0] |
| conv4 block5 0 bn (BatchNormali | (None, 62, 12, 384) | 1536 | conv4 block4 concat[0][0] |
| conv4 block5 0 relu (Activation | (None, 62, 12, 384) | 0 | conv4 block5 0 bn[0][0] |
| conv4 block5 1 conv (Conv2D) | (None, 62, 12, 128) | 49152 | conv4 block5 0 relu[0][0] |
| conv4 block5 1 bn (BatchNormali | (None, 62, 12, 128) | 512 | conv4 block5 1 conv[0][0] |
| conv4 block5 1 relu (Activation | (None, 62, 12, 128) | 0 | conv4 block5 1 bn[0][0] |
| conv4 block5 2 conv (Conv2D) | (None, 62, 12, 32) | 12288 | conv4 block5 1 relu[0][0] |
| conv4 block5 concat (Concatenat | (None, 62, 12, 416) | 0 | conv4 block4 concat[0][0] |
| | | | conv4 block5 2 conv[0][0] |
| conv4 block6 0 bn (BatchNormali | (None, 62, 12, 416) | 1664 | conv4 block5 concat[0][0] |
| conv4 block6 0 relu (Activation | (None, 62, 12, 416) | 0 | conv4 block6 0 bn[0][0] |
| conv4 block6 1 conv (Conv2D) | (None, 62, 12, 128) | 53248 | conv4 block6 0 relu[0][0] |
| conv4 block6 1 bn (BatchNormali | (None, 62, 12, 128) | 512 | conv4 block6 1 conv[0][0] |
| conv4 block6 1 relu (Activation | (None, 62, 12, 128) | 0 | conv4 block6 1 bn[0][0] |
| conv4 block6 2 conv (Conv2D) | (None, 62, 12, 32) | 12288 | conv4 block6 1 relu[0][0] |
| conv4 block6 concat (Concatenat | (None, 62, 12, 448) | 0 | conv4 block5 concat[0][0] |
| | | | conv4 block6 2 conv[0][0] |
| conv4 block7 0 bn (BatchNormali | (None, 62, 12, 448) | 1792 | conv4 block6 concat[0][0] |
| conv4 block7 0 relu (Activation | (None, 62, 12, 448) | 0 | conv4 block7 0 bn[0][0] |
| conv4 block7 1 conv (Conv2D) | (None, 62, 12, 128) | 57344 | conv4 block7 0 relu[0][0] |
| conv4 block7 1 bn (BatchNormali | (None, 62, 12, 128) | 512 | conv4 block7 1 conv[0][0] |
| conv4 block7 1 relu (Activatio | (None, 62, 12, 128) | 0 | conv4 block7 1 bn[0][0] |
| conv4 block7 2 conv (Conv2D) | (None, 62, 12, 32) | 12288 | conv4 block7 1 relu[0][0] |
| conv4 block7 concat (Concatenat | (None, 62, 12, 480) | 0 | conv4 block6 concat[0][0] |
| | | | conv4 block7 2 conv[0][0] |
| conv4 block8 0 bn (BatchNormali | (None, 62, 12, 480) | 1920 | conv4 block7 concat[0][0] |
| conv4 block8 0 relu (Activation | (None, 62, 12, 480) | 0 | conv4 block8 0 bn[0][0] |
| conv4 block8 1 conv (Conv2D) | (None, 62, 12, 128) | 61440 | conv4 block8 0 relu[0][0] |
| conv4 block8 1 bn (BatchNormali | (None, 62, 12, 128) | 512 | conv4 block8 1 conv[0][0] |
| conv4 block8 1 relu (Activation | (None, 62, 12, 128) | 0 | conv4 block8 1 bn[0][0] |
| conv4 block8 2 conv (Conv2D) | (None, 62, 12, 32) | 12288 | conv4 block8 1 relu[0][0] |
| conv4 block8 concat (Concatenat | (None, 62, 12, 512) | 0 | conv4 block7 concat[0][0] |
| | | | conv4 block8 2 conv[0][0] |
| conv4 block9 0 bn (BatchNormali | (None, 62, 12, 512) | 2048 | conv4 block8 concat[0][0] |
| conv4 block9 0 relu (Activation | (None, 62, 12, 512) | 0 | conv4 block9 0 bn[0][0] |
| conv4 block9 1 conv (Conv2D) | (None, 62, 12, 128) | 65536 | conv4 block9 0 relu[0][0] |
| conv4 block9 1 bn (BatchNormali | (None, 62, 12, 128) | 512 | conv4 block9 1 conv[0][0] |
| conv4 block9 1 relu (Activation | (None, 62, 12, 128) | 0 | conv4 block9 1 bn[0][0] |
| conv4 block9 2 conv (Conv2D) | (None, 62, 12, 32) | 12288 | conv4 block9 1 relu[0][0] |
| conv4 block9 concat (Concatenat | (None, 62, 12, 544) | 0 | conv4 block8 concat[0][0] |
| | | | conv4 block9 2 conv[0][0] |
| conv4 block10 0 bn (BatchNormal | (None, 62, 12, 544) | 2176 | conv4 block9 concat[0][0] |
| conv4 block10 0 relu (Activatio | (None, 62, 12, 544) | 0 | conv4 block10 0 bn[0][0] |
| conv4 block10 1 conv (Conv2D) | (None, 62, 12, 128) | 69632 | conv4 block10 0 relu[0][0] |
| conv4 block10 1 bn (BatchNormal | (None, 62, 12, 128) | 512 | conv4 block10 1 conv[0][0] |
| conv4 block10 1 relu (Activatio | (None, 62, 12, 128) | 0 | conv4 block10 1 bn[0][0] |
| conv4 block10 2 conv (Conv2D) | (None, 62, 12, 32) | 12288 | conv4 block10 1 relu[0][0] |
| conv4 block10 concat (Concatena | (None, 62, 12, 576) | 0 | conv4 block9 concat[0][0] |
| | | | conv4 block10 2 conv[0][0] |
| conv4 block11 0 bn (BatchNormal | (None, 62, 12, 576) | 2304 | conv4 block10 concat[0][0] |
| conv4 block11 0 relu (Activatio | (None, 62, 12, 576) | 0 | conv4 block11 0 bn[0][0] |
| conv4 block11 1 conv (Conv2D) | (None, 62, 12, 128) | 73728 | conv4 block11 0 relu[0][0] |
| conv4 block11 1 bn (BatchNormal | (None, 62, 12, 128) | 512 | conv4 block11 1 conv[0][0] |
| conv4 block11 1 relu (Activatio | (None, 62, 12, 128) | 0 | conv4 block11 1 bn[0][0] |
| conv4 block11 2 conv (Conv2D) | (None, 62, 12, 32) | 12288 | conv4 block11 1 relu[0][0] |
| conv4 block11 concat (Concatena | (None, 62, 12, 608) | 0 | conv4 block10 concat[0][0] |
| | | | conv4 block11 2 conv[0][0] |
| conv4 block12 0 bn (BatchNormal | (None, 62, 12, 608) | 2432 | conv4 block11 concat[0][0] |
| conv4 block12 0 relu (Activatio | (None, 62, 12, 608) | 0 | conv4 block12 0 bn[0][0] |
| conv4 block12 1 conv (Conv2D) | (None, 62, 12, 128) | 77824 | conv4 block12 0 relu[0][0] |
| conv4 block12 1 bn (BatchNormal | (None, 62, 12, 128) | 512 | conv4 block12 1 conv[0][0] |

TABLE 8-continued

Model: "Densenet"

| Layer (type) | Output Shape | Param # | Connected to |
|---|---|---|---|
| conv4 block12 1 relu (Activatio | (None, 62, 12, 128) | 0 | conv4 block12 1 bn[0][0] |
| conv4 block12 2 conv (Conv2D) | (None, 62, 12, 32) | 12288 | conv4 block12 1 relu[0][0] |
| conv4 block12 concat (Concatena | (None, 62, 12, 640) | 0 | conv4 block11 concat[0][0] |
| | | | conv4 block12 2 conv[0][0] |
| conv4 block13 0 bn (BatchNormal | (None, 62, 12, 640) | 2560 | conv4 block12 concat[0][0] |
| conv4 block13 0 relu (Activatio | (None, 62, 12, 640) | 0 | conv4 block13 0 bn[0][0] |
| conv4 block13 1 conv (Conv2D) | (None, 62, 12, 128) | 81920 | conv4 block13 0 relu[0][0] |
| conv4 block13 1 bn (BatchNormal | (None, 62, 12, 128) | 512 | conv4 block13 1 conv[0][0] |
| conv4 block13 1 relu (Activatio | (None, 62, 12, 128) | 0 | conv4 block13 1 bn[0][0] |
| conv4 block13 2 conv (Conv2D) | (None, 62, 12, 32) | 12288 | conv4 block13 1 relu[0][0] |
| conv4 block13 concat (Concatena | (None, 62, 12, 672) | 0 | conv4 block12 concat[0][0] |
| | | | conv4 block13 2 conv[0][0] |
| conv4 block14 0 bn (BatchNormal | (None, 62, 12, 672) | 2688 | conv4 block13 concat[0][0] |
| conv4 block14 0 relu (Activatio | (None, 62, 12, 672) | 0 | conv4 block14 0 bn[0][0] |
| conv4 block14 1 conv (Conv2D) | (None, 62, 12, 128) | 86016 | conv4 block14 0 relu[0][0] |
| conv4 block14 1 bn (BatchNormal | (None, 62, 12, 128) | 512 | conv4 block14 1 conv[0][0] |
| conv4 block14 1 relu (Activatio | (None, 62, 12, 128) | 0 | conv4 block14 1 bn[0][0] |
| conv4 block14 2 conv (Conv2D) | (None, 62, 12, 32) | 12288 | conv4 block14 1 relu[0][0] |
| conv4 block14 concat (Concatena | (None, 62, 12, 704) | 0 | conv4 block13 concat[0][0] |
| | | | conv4 block14 2 conv[0][0] |
| conv4 block15 0 bn (BatchNormal | (None, 62, 12, 704) | 2816 | conv4 block14 concat[0][0] |
| conv4 block15 0 relu (Activatio | (None, 62, 12, 704) | 0 | conv4 block15 0 bn[0][0] |
| conv4 block15 1 conv (Conv2D) | (None, 62, 12, 128) | 90112 | conv4 block15 0 relu[0][0] |
| conv4 block15 1 bn (BatchNormal | (None, 62, 12, 128) | 512 | conv4 block15 1 conv[0][0] |
| conv4 block15 1 relu (Activatio | (None, 62, 12, 128) | 0 | conv4 block15 1 bn[0][0] |
| conv4 block15 2 conv (Conv2D) | (None, 62, 12, 32) | 12288 | conv4 block15 1 relu[0][0] |
| conv4 block15 concat (Concatena | (None, 62, 12, 736) | 0 | conv4 block14 concat[0][0] |
| | | | conv4 block15 2 conv[0][0] |
| conv4 block16 0 bn (BatchNormal | (None, 62, 12, 736) | 2944 | conv4 block15 concat[0][0] |
| conv4 block16 0 relu (Activatio | (None, 62, 12, 736) | 0 | conv4 block16 0 bn[0][0] |
| conv4 block16 1 conv (Conv2D) | (None, 62, 12, 128) | 94208 | conv4 block16 0 relu[0][0] |
| conv4 block16 1 bn (BatchNormal | (None, 62, 12, 128) | 512 | conv4 block16 1 conv[0][0] |
| conv4 block16 1 relu (Activatio | (None, 62, 12, 128) | 0 | conv4 block16 1 bn[0][0] |
| conv4 block16 2 conv (Conv2D) | (None, 62, 12, 32) | 12288 | conv4 block16 1 relu[0][0] |
| conv4 block16 concat (Concatena | (None, 62, 12, 768) | 0 | conv4 block15 concat[0][0] |
| | | | conv4 block16 2 conv[0][0] |
| conv4 block17 0 bn (BatchNormal | (None, 62, 12, 768) | 3072 | conv4 block16 concat[0][0] |
| conv4 block17 0 relu (Activatio | (None, 62, 12, 768) | 0 | conv4 block17 0 bn[0][0] |
| conv4 block17 1 conv (Conv2D) | (None, 62, 12, 128) | 98304 | conv4 block17 0 relu[0][0] |
| conv4 block17 1 bn (BatchNormal | (None, 62, 12, 128) | 512 | conv4 block17 1 conv[0][0] |
| conv4 block17 1 relu (Activatio | (None, 62, 12, 128) | 0 | conv4 block17 1 bn[0][0] |
| conv4 block17 2 conv (Conv2D) | (None, 62, 12, 32) | 12288 | conv4 block17 1 relu[0][0] |
| conv4 block17 concat (Concatena | (None, 62, 12, 800) | 0 | conv4 block16 concat[0][0] |
| | | | conv4 block17 2 conv[0][0] |
| conv4 block18 0 bn (BatchNormal | (None, 62, 12, 800) | 3200 | conv4 block17 concat[0][0] |
| conv4 block18 0 relu (Activatio | (None, 62, 12, 800) | 0 | conv4 block18 0 bn[0][0] |
| conv4 block18 1 conv (Conv2D) | (None, 62, 12, 128) | 102400 | conv4 block18 0 relu[0][0] |
| conv4 block18 1 bn (BatchNormal | (None, 62, 12, 128) | 512 | conv4 block18 1 conv[0][0] |
| conv4 block18 1 relu (Activatio | (None, 62, 12, 128) | 0 | conv4 block18 1 bn[0][0] |
| conv4 block18 2 conv (Conv2D) | (None, 62, 12, 32) | 12288 | conv4 block18 1 relu[0][0] |
| conv4 block18 concat (Concatena | (None, 62, 12, 832) | 0 | conv4 block17 concat[0][0] |
| | | | conv4 block18 2 conv[0][0] |
| conv4 block19 0 bn (BatchNormal | (None, 62, 12, 832) | 3328 | conv4 block18 concat[0][0] |
| conv4 block19 0 relu (Activatio | (None, 62, 12, 832) | 0 | conv4 block19 0 bn[0][0] |
| conv4 block19 1 conv (Conv2D) | (None, 62, 12, 128) | 106496 | conv4 block19 0 relu[0][0] |
| conv4 block19 1 bn (BatchNormal | (None, 62, 12, 128) | 512 | conv4 block19 1 conv[0][0] |
| conv4 block19 1 relu (Activatio | (None, 62, 12, 128) | 0 | conv4 block19 1 bn[0][0] |
| conv4 block19 2 conv (Conv2D) | (None, 62, 12, 32) | 12288 | conv4 block19 1 relu[0][0] |
| conv4 block19 concat (Concatena | (None, 62, 12, 864) | 0 | conv4 block18 concat[0][0] |
| | | | conv4 block19 2 conv[0][0] |
| conv4 block20 0 bn (BatchNormal | (None, 62, 12, 864) | 3456 | conv4 block19 concat[0][0] |
| conv4 block20 0 relu (Activatio | (None, 62, 12, 864) | 0 | conv4 block20 0 bn[0][0] |
| conv4 block20 1 conv (Conv2D) | (None, 62, 12, 128) | 110592 | conv4 block20 0 relu[0][0] |
| conv4 block20 1 bn (BatchNormal | (None, 62, 12, 128) | 512 | conv4 block20 1 conv[0][0] |
| conv4 block20 1 relu (Activatio | (None, 62, 12, 128) | 0 | conv4 block20 1 bn[0][0] |
| conv4 block20 2 conv (Conv2D) | (None, 62, 12, 32) | 12288 | conv4 block20 1 relu[0][0] |
| conv4 block20 concat (Concatena | (None, 62, 12, 896) | 0 | conv4 block19 concat[0][0] |
| | | | conv4 block20 2 conv[0][0] |
| conv4 block21 0 bn (BatchNormal | (None, 62, 12, 896) | 3584 | conv4 block20 concat[0][0] |
| conv4 block21 0 relu (Activatio | (None, 62, 12, 896) | 0 | conv4 block21 0 bn[0][0] |
| conv4 block21l conv (Conv2D) | (None, 62, 12, 128) | 114688 | conv4 block21 0 relu[0][0] |
| conv4 block21l bn (BatchNormal | (None, 62, 12, 128) | 512 | conv4 block21 1 conv[0][0] |
| conv4 block21l relu (Activatio | (None, 62, 12, 128) | 0 | conv4 block21 1 bn[0][0] |
| conv4 block21 2 conv (Conv2D) | (None, 62, 12, 32) | 12288 | conv4 block21 1 relu[0][0] |
| conv4 block21 concat (Concatena | (None, 62, 12, 928) | 0 | conv4 block20 concat[0][0] |
| | | | conv4 block21 2 conv[0][0] |

TABLE 8-continued

Model: "Densenet"

| Layer (type) | Output Shape | Param # | Connected to |
|---|---|---|---|
| conv4 block22 0 bn (BatchNormal | (None, 62, 12, 928) | 3712 | conv4 block21 concat[0][0] |
| conv4 block22 0 relu (Activatio | (None, 62, 12, 928) | 0 | conv4 block22 0 bn[0][0] |
| conv4 block22 1 conv (Conv2D) | (None, 62, 12, 128) | 118784 | conv4 block22 0 relu[0][0] |
| conv4 block22 1 bn (BatchNormal | (None, 62, 12, 128) | 512 | conv4 block22 1 conv[0][0] |
| conv4 block22 1 relu (Activatio | (None, 62, 12, 128) | 0 | conv4 block22 1 bn[0][0] |
| conv4 block22 2 conv (Conv2D) | (None, 62, 12, 32) | 12288 | conv4 block22 1 relu[0][0] |
| conv4 block22 concat (Concatena | (None, 62, 12, 960) | 0 | conv4 block21 concat[0][0] |
| | | | conv4 block22 2 conv[0][0] |
| conv4 block23 0 bn (BatchNormal | (None, 62, 12, 960) | 3840 | conv4 block22 concat[0][0] |
| conv4 block23 0 relu (Activatio | (None, 62, 12, 960) | 0 | conv4 block23 0 bn[0][0] |
| conv4 block23 1 conv (Conv2D) | (None, 62, 12, 128) | 122880 | conv4 block23 0 relu[0][0] |
| conv4 block23 1 bn (BatchNormal | (None, 62, 12, 128) | 512 | conv4 block23 1 conv[0][0] |
| conv4 block23 1 relu (Activatio | (None, 62, 12, 128) | 0 | conv4 block23 1 bn[0][0] |
| conv4 block23 2 conv (Conv2D) | (None, 62, 12, 32) | 12288 | conv4 block23 1 relu[0][0] |
| conv4 block23 concat (Concatena | (None, 62, 12, 992) | 0 | conv4 block22 concat[0][0] |
| | | | conv4 block23 2 conv[0][0] |
| conv4 block24 0 bn (BatchNormal | (None, 62, 12, 992) | 3968 | conv4 block23 concat[0][0] |
| conv4 block24 0 relu (Activatio | (None, 62, 12, 992) | 0 | conv4 block24 0 bn[0][0] |
| conv4 block24 1 conv (Conv2D) | (None, 62, 12, 128) | 126976 | conv4 block24 0 relu[0][0] |
| conv4 block24 1 bn (BatchNormal | (None, 62, 12, 128) | 512 | conv4 block24 1 conv[0][0] |
| conv4 block24 1 relu (Activatio | (None, 62, 12, 128) | 0 | conv4 block24 1 bn[0][0] |
| conv4 block24 2 conv (Conv2D) | (None, 62, 12, 32) | 12288 | conv4 block24 1 relu[0][0] |
| conv4 block24 concat (Concatena | (None, 62, 12, 1024) | 0 | conv4 block23 concat[0][0] |
| | | | conv4 block24 2 conv[0][0] |
| pool4bn (BatchNormalization) | (None, 62, 12, 1024) | 4096 | conv4 block24 concat[0][0] |
| pool4 relu (Activation) | (None, 62, 12, 1024) | 0 | pool4 bn[0][0] |
| pool4 conv (Conv2D) | (None, 62, 12, 512) | 524288 | pool4 relu[0][0] |
| pool4 pool (AveragePooling2D) | (None, 31, 12, 512) | 0 | pool4 conv[0][0] |
| conv5 block1 0 bn (BatchNormali | (None, 31, 12, 512) | 2048 | pool4 pool[0][0] |
| conv5 block1 0 relu (Activation | (None, 31, 12, 512) | 0 | conv5 block1 0 bn[0][0] |
| conv5 block1 1 conv (Conv2D) | (None, 31, 12, 128) | 65536 | conv5 block1 0 relu[0][0] |
| conv5 block1 1 bn (BatchNormali | (None, 31, 12, 128) | 512 | conv5 block1 1 conv[0][0] |
| conv5 block1 1 relu (Activation | (None, 31, 12, 128) | 0 | conv5 block1 1 bn[0][0] |
| conv5 block1 2 conv (Conv2D) | (None, 31, 12, 32) | 12288 | conv5 block1 1 relu[0][0] |
| conv5 block1 concat (Concatenat | (None, 31, 12, 544) | 0 | pool4 pool[0][0] |
| | | | conv5 block1 2 conv[0][0] |
| conv5 block2 0 bn (BatchNormali | (None, 31, 12, 544) | 2176 | conv5 block1 concat[0][0] |
| conv5 block2 0 relu (Activation | (None, 31, 12, 544) | 0 | conv5 block2 0 bn[0][0] |
| conv5 block2 1 conv (Conv2D) | (None, 31, 12, 128) | 69632 | conv5 block2 0 relu[0][0] |
| conv5 block2 1 bn (BatchNormali | (None, 31, 12, 128) | 512 | conv5 block2 1 conv[0][0] |
| conv5 block2 1 relu (Activation | (None, 31, 12, 128) | 0 | conv5 block2 1 bn[0][0] |
| conv5 block2 2 conv (Conv2D) | (None, 31, 12, 32) | 12288 | conv5 block2 1 relu[0][0] |
| conv5 block2 concat (Concatenat | (None, 31, 12, 576) | 0 | conv5 block1 concat[0][0] |
| | | | conv5 block2 2 conv[0][0] |
| conv5 block3 0 bn (BatchNormali | (None, 31, 12, 576) | 2304 | conv5 block2 concat[0][0] |
| conv5 block3 0 relu (Activation | (None, 31, 12, 576) | 0 | conv5 block3 0 bn[0][0] |
| conv5 block3 1 conv (Conv2D) | (None, 31, 12, 128) | 73728 | conv5 block3 0 relu[0][0] |
| conv5 block3 1 bn (BatchNormali | (None, 31, 12, 128) | 512 | conv5 block3 1 conv[0][0] |
| conv5 block3 1 relu (Activation | (None, 31, 12, 128) | 0 | conv5 block3 1 bn[0][0] |
| conv5 block3 2 conv (Conv2D) | (None, 31, 12, 32) | 12288 | conv5 block3 1 relu[0][0] |
| conv5 block3 concat (Concatenat | (None, 31, 12, 608) | 0 | conv5 block2 concat[0][0] |
| | | | conv5 block3 2 conv[0][0] |
| conv5 block4 0 bn (BatchNormali | (None, 31, 12, 608) | 2432 | conv5 block3 concat[0][0] |
| conv5 block4 0 relu (Activation | (None, 31, 12, 608) | 0 | conv5 block4 0 bn[0][0] |
| conv5 block4 1 conv (Conv2D) | (None, 31, 12, 128) | 77824 | conv5 block4 0 relu[0][0] |
| conv5 block4 1 bn (BatchNormali | (None, 31, 12, 128) | 512 | conv5 block4 1 conv[0][0] |
| conv5 block4 1 relu (Activation | (None, 31, 12, 128) | 0 | conv5 block4 1 bn[0][0] |
| conv5 block4 2 conv (Conv2D) | (None, 31, 12, 32) | 12288 | conv5 block4 1 relu[0][0] |
| conv5 block4 concat (Concatenat | (None, 31, 12, 640) | 0 | conv5 block3 concat[0][0] |
| | | | conv5 block4 2 conv[0][0] |
| conv5 block5 0 bn (BatchNormali | (None, 31, 12, 640) | 2560 | conv5 block4 concat[0][0] |
| conv5 block5 0 relu (Activation | (None, 31, 12, 640) | 0 | conv5 block5 0 bn[0][0] |
| conv5 block5 1 conv (Conv2D) | (None, 31, 12, 128) | 81920 | conv5 block5 0 relu[0][0] |
| conv5 block5 1 bn (BatchNormali | (None, 31, 12, 128) | 512 | conv5 block5 1 conv[0][0] |
| conv5 block5 1 relu (Activation | (None, 31, 12, 128) | 0 | conv5 block5 1 bn[0][0] |
| conv5 block5 2 conv (Conv2D) | (None, 31, 12, 32) | 12288 | conv5 block5 1 relu[0][0] |
| conv5 block5 concat (Concatenat | (None, 31, 12, 672) | 0 | conv5 block4 concat[0][0] |
| | | | conv5 block5 2 conv[0][0] |
| conv5 block6 0 bn (BatchNormali | (None, 31, 12, 672) | 2688 | conv5 block5 concat[0][0] |
| conv5 block6 0 relu (Activation | (None, 31, 12, 672) | 0 | conv5 block6 0 bn[0][0] |
| conv5 block6 1 conv (Conv2D) | (None, 31, 12, 128) | 86016 | conv5 block6 0 relu[0][0] |
| conv5 block6 1 bn (BatchNormali | (None, 31, 12, 128) | 512 | conv5 block6 1 conv[0][0] |
| conv5 block6 1 relu (Activation | (None, 31, 12, 128) | 0 | conv5 block6 1 bn[0][0] |
| conv5 block6 2 conv (Conv2D) | (None, 31, 12, 32) | 12288 | conv5 block6 1 relu[0][0] |
| conv5 block6 concat (Concatenat | (None, 31, 12, 704) | 0 | conv5 block5 concat[0][0] |
| | | | conv5 block6 2 conv[0][0] |

TABLE 8-continued

Model: "Densenet"

| Layer (type) | Output Shape | Param # | Connected to |
|---|---|---|---|
| conv5 block7 0 bn (BatchNormali | (None, 31, 12, 704) | 2816 | conv5 block6 concat[0][0] |
| conv5 block7 0 relu (Activation | (None, 31, 12, 704) | 0 | conv5 block7 0 bn[0][0] |
| conv5 block7 1 conv (Conv2D) | (None, 31, 12, 128) | 90112 | conv5 block7 0 relu[0][0] |
| conv5 block7 1 bn (BatchNormali | (None, 31, 12, 128) | 512 | conv5 block7 1 conv[0][0] |
| conv5 block7 1 relu (Activation | (None, 31, 12, 128) | 0 | conv5 block7 1 bn[0][0] |
| conv5 block7 2 conv (Conv2D) | (None, 31, 12, 32) | 12288 | conv5 block7 1 relu[0][0] |
| conv5 block7 concat (Concatenat | (None, 31, 12, 736) | 0 | conv5 block6 concat[0][0] |
| | | | conv5 block7 2 conv[0][0] |
| conv5 block8 0 bn (BatchNormali | (None, 31, 12, 736) | 2944 | conv5 block7 concat[0][0] |
| conv5 block8 0 relu (Activation | (None, 31, 12, 736) | 0 | conv5 block8 0 bn[0][0] |
| conv5 block8 1 conv (Conv2D) | (None, 31, 12, 128) | 94208 | conv5 block8 0 relu[0][0] |
| conv5 block8 1 bn (BatchNormali | (None, 31, 12, 128) | 512 | conv5 block8 1 conv[0][0] |
| conv5 block8 1 relu (Activation | (None, 31, 12, 128) | 0 | conv5 block8 1 bn[0][0] |
| conv5 block8 2 conv (Conv2D) | (None, 31, 12, 32) | 12288 | conv5 block8 1 relu[0][0] |
| conv5 block8 concat (Concatenat | (None, 31, 12, 768) | 0 | conv5 block8 concat[0][0] |
| | | | conv5 block8 2 conv[0][0] |
| conv5 block9 0 bn (BatchNormali | (None, 31, 12, 768) | 3072 | conv5 block8 concat[0][0] |
| conv5 block9 0 relu (Activation | (None, 31, 12, 768) | 0 | conv5 block9 0 bn[0][0] |
| conv5 block9 1 conv (Conv2D) | (None, 31, 12, 128) | 98304 | conv5 block9 0 relu[0][0] |
| conv5 block9 1 bn (BatchNormali | (None, 31, 12, 128) | 512 | conv5 block9 1 conv[0][0] |
| conv5 block9 1 relu (Activation | (None, 31, 12, 128) | 0 | conv5 block9 1 bn[0][0] |
| conv5 block9 2 conv (Conv2D) | (None, 31, 12, 32) | 12288 | conv5 block9 1 relu[0][0] |
| conv5 block9 concat (Concatenat | (None, 31, 12, 800) | 0 | conv5 block8 concat[0][0] |
| | | | conv5 block9 2 conv[0][0] |
| conv5 block10 0 bn (BatchNormal | (None, 31, 12, 800) | 3200 | conv5 block9 concat[0][0] |
| conv5 block10 0 relu (Activatio | (None, 31, 12, 800) | 0 | conv5 block10 0 bn[0][0] |
| conv5 block10 1 conv (Conv2D) | (None, 31, 12, 128) | 102400 | conv5 block10 0 relu[0][0] |
| conv5 block10 1 bn (BatchNormal | (None, 31, 12, 128) | 512 | conv5 block10 1 conv[0][0] |
| conv5 block10 1 relu (Activatio | (None, 31, 12, 128) | 0 | conv5 block10 1 bn[0][0] |
| conv5 block10 2 conv (Conv2D) | (None, 31, 12, 32) | 12288 | conv5 block10 1 relu[0][0] |
| conv5 block10 concat (Concatena | (None, 31, 12, 832) | 0 | conv5 block9 concat[0][0] |
| | | | conv5 block10 2 conv[0][0] |
| conv5 block11 0 bn (BatchNormal | (None, 31, 12, 832) | 3328 | conv5 block10 concat[0][0] |
| conv5 block11 0 relu (Activatio | (None, 31, 12, 832) | 0 | conv5 block11 0 bn[0][0] |
| conv5 block11 1 conv (Conv2D) | (None, 31, 12, 128) | 106496 | conv5 block11 0 relu[0][0] |
| conv5 block11 1 bn (BatchNormal | (None, 31, 12, 128) | 512 | conv5 block11 1 conv[0][0] |
| conv5 block11 1 relu (Activatio | (None, 31, 12, 128) | 0 | conv5 block11 1 bn[0][0] |
| conv5 block11 2 conv (Conv2D) | (None, 31, 12, 32) | 12288 | conv5 block11 1 relu[0][0] |
| conv5 block11 concat (Concatena | (None, 31, 12, 864) | 0 | conv5 block10 concat[0][0] |
| | | | conv5 block11 2 conv[0][0] |
| conv5 block12 0 bn (BatchNormal | (None, 31, 12, 864) | 3456 | conv5 block11 concat[0][0] |
| conv5 block12 0 relu (Activatio | (None, 31, 12, 864) | 0 | conv5 block12 0 bn[0][0] |
| conv5 block12 1 conv (Conv2D) | (None, 31, 12, 128) | 110592 | conv5 block12 0 relu[0][0] |
| conv5 block12 1 bn (BatchNormal | (None, 31, 12, 128) | 512 | conv5 block12 1 conv[0][0] |
| conv5 block12 1 relu (Activatio | (None, 31, 12, 128) | 0 | conv5 block12 1 bn[0][0] |
| conv5 block12 2 conv (Conv2D) | (None, 31, 12, 32) | 12288 | conv5 block12 1 relu[0][0] |
| conv5 block12 concat (Concatena | (None, 31, 12, 896) | 0 | conv5 block11 concat[0][0] |
| | | | conv5 block12 2 conv[0][0] |
| conv5 block13 0 bn (BatchNormal | (None, 31, 12, 896) | 3584 | conv5 block12 concat[0][0] |
| conv5 block13 0 relu (Activatio | (None, 31, 12, 896) | 0 | conv5 block13 0 bn[0][0] |
| conv5 block13 1 conv (Conv2D) | (None, 31, 12, 128) | 114688 | conv5 block13 0 relu[0][0] |
| conv5 block13 1 bn (BatchNormal | (None, 31, 12, 128) | 512 | conv5 block13 1 conv[0][0] |
| conv5 block13 1 relu (Activatio | (None, 31, 12, 128) | 0 | conv5 block13 1 bn[0][0] |
| conv5 block13 2 conv (Conv2D) | (None, 31, 12, 32) | 12288 | conv5 block13 1 relu[0][0] |
| conv5 block13 concat (Concatena | (None, 31, 12, 928) | 0 | conv5 block12 concat[0][0] |
| | | | conv5 block13 2 conv[0][0] |
| conv5 block14 0 bn (BatchNormal | (None, 31, 12, 928) | 3712 | conv5 block13 concat[0][0] |
| conv5 block14 0 relu (Activatio | (None, 31, 12, 928) | 0 | conv5 block14 0 bn[0][0] |
| conv5 block14 1 conv (Conv2D) | (None, 31, 12, 128) | 118784 | conv5 block14 0 relu[0][0] |
| conv5 block14 1 bn (BatchNormal | (None, 31, 12, 128) | 512 | conv5 block14 1 conv[0][0] |
| conv5 block14 1 relu (Activatio | (None, 31, 12, 128) | 0 | conv5 block14 1 bn[0][0] |
| conv5 block14 2 conv (Conv2D) | (None, 31, 12, 32) | 12288 | conv5 block14 1 relu[0][0] |
| conv5 block14 concat (Concatena | (None, 31, 12, 960) | 0 | conv5 block13 concat[0][0] |
| | | | conv5 block14 2 conv[0][0] |
| conv5 block15 0 bn (BatchNormal | (None, 31, 12, 960) | 3840 | conv5 block14 concat[0][0] |
| conv5 block15 0 relu (Activatio | (None, 31, 12, 960) | 0 | conv5 block15 0 bn[0][0] |
| conv5 block15 1 conv (Conv2D) | (None, 31, 12, 128) | 122880 | conv5 block15 0 relu[0][0] |
| conv5 block15 1 bn (BatchNormal | (None, 31, 12, 128) | 512 | conv5 block15 1 conv[0][0] |
| conv5 block15 1 relu (Activatio | (None, 31, 12, 128) | 0 | conv5 block15 1 bn[0][0] |
| conv5 block15 2 conv (Conv2D) | (None, 31, 12, 32) | 12288 | conv5 block15 1 relu[0][0] |
| conv5 block15 concat (Concatena | (None, 31, 12, 992) | 0 | conv5 block14 concat[0][0] |
| | | | conv5 block15 2 conv[0][0] |
| conv5 block16 0 bn (BatchNormal | (None, 31, 12, 992) | 3968 | conv5 block15 concat[0][0] |
| conv5 block16 0 relu (Activatio | (None, 31, 12, 992) | 0 | conv5 block16 0 bn[0][0] |
| conv5 block16 1 conv (Conv2D) | (None, 31, 12, 128) | 126976 | conv5 block16 0 relu[0][0] |
| conv5 block16 1 bn (BatchNormal | (None, 31, 12, 128) | 512 | conv5 block16 1 conv[0][0] |

TABLE 8-continued

| Model: "Densenet" | | | |
|---|---|---|---|
| Layer (type) | Output Shape | Param # | Connected to |
| conv5 block16 1 relu (Activatio | (None, 31, 12, 128) | 0 | conv5 block16 1 bn[0][0] |
| conv5 block16 2 conv (Conv2D) | (None, 31, 12, 32) | 12288 | conv5 block16 1 relu[0][0] |
| conv5 block16 concat (Concatena | (None, 31, 12, 1024) | 0 | conv5 block15 concat[0][0] |
| | | | conv5 block16 2 conv[0][0] |
| bn (BatchNormalization) | (None, 31, 12, 1024) | 4096 | conv5 block16 concat[0][0] |
| max pool (GlobalMaxPooling2D) | (None, 1024) | 0 | bn[0][0] |
| | Total params: 5,603,136 | | |
| | Trainable params: 5,519,488 | | |
| | Non-trainable params: 83,648 | | |

APPENDIX E

TABLE 9

| Model: "HEARTio" | | | |
|---|---|---|---|
| Layer (type) | Output Shape | Param # | Connected to |
| input 2 (InputLayer) | (None, 1000, 12, 1) | 0 | |
| Encoder (Model) | (None, 1024) | 13451936 | input 2[0][0] |
| | | | lead mask 1[0][0] |
| | | | lead mask 2[0][0] |
| | | | lead mask 3[0][0] |
| | | | lead mask 4[0][0] |
| | | | lead mask 5[0][0] |
| | | | lead mask 6[0][0] |
| | | | lead mask 7[0][0] |
| | | | lead mask 8[0][0] |
| | | | lead mask 9[0][0] |
| | | | lead mask 10[0][0] |
| | | | lead mask 11[0][0] |
| | | | lead mask 12[0][0] |
| Greater Decoder (Model) | (None, 1000, 12, 1) | 13324802 | Encoder[2][0] |
| densenet121 (Model) | (None, 1024) | 5603136 | Greater Decoder[1][0] |
| concatenate 1 (Concatenate) | (None, 2048) | 0 | Encoder[2][0] |
| | | | densenet121[1][0] |
| lead mask 1 (LeadMask) | (None, 1000, 12, 1) | 0 | Greater Decoder[1][0] |
| lead mask 2 (LeadMask) | (None, 1000, 12, 1) | 0 | Greater Decoder[1][0] |
| lead mask 3 (LeadMask) | (None, 1000, 12, 1) | 0 | Greater Decoder[1][0] |
| lead mask 4 (LeadMask) | (None, 1000, 12, 1) | 0 | Greater Decoder[1][0] |
| lead mask 5 (LeadMask) | (None, 1000, 12, 1) | 0 | Greater Decoder[1][0] |
| lead mask 6 (LeadMask) | (None, 1000, 12, 1) | 0 | Greater Decoder[1][0] |
| lead mask 7 (LeadMask) | (None, 1000, 12, 1) | 0 | Greater Decoder[1][0] |
| lead mask 8 (LeadMask) | (None, 1000, 12, 1) | 0 | Greater Decoder[1][0] |
| lead mask 9 (LeadMask) | (None, 1000, 12, 1) | 0 | Greater Decoder[1][0] |
| lead mask 10 (LeadMask) | (None, 1000, 12, 1) | 0 | Greater Decoder[1][0] |
| lead mask 11 (LeadMask) | (None, 1000, 12, 1) | 0 | Greater Decoder[1][0] |
| lead mask 12 (LeadMask) | (None, 1000, 12, 1) | 0 | Greater Decoder[1][0] |
| dropout 5 (Dropout) | (None, 2048) | 0 | concatenate 1[0][0] |
| gaussian noise 1 (GaussianNoise | (None, 2048) | 0 | concatenate 1[0][0] |
| dense 9 (Dense) | (None, 4) | 8196 | dropout 5[0][0] |
| dense 3 (Dense) | (None, 4) | 8196 | gaussian noise 1[0][0] |
| dropout 1 (Dropout) | (None, 2048) | 0 | concatenate 1[0][0] |
| dropout 2 (Dropout) | (None, 2048) | 0 | concatenate 1[0][0] |
| dropout 3 (Dropout) | (None, 2048) | 0 | concatenate 1[0][0] |
| gaussian noise 2 (GaussianNoise | (None, 2048) | 0 | concatenate 1[0][0] |
| dropout 4 (Dropout) | (None, 2048) | 0 | concatenate 1[0][0] |
| dropout 6 (Dropout) | (None, 1024) | 0 | Encoder[3][0] |
| dropout 7 (Dropout) | (None, 1024) | 0 | Encoder[4][0] |
| dropout 8 (Dropout) | (None, 1024) | 0 | Encoder[5][0] |
| dropout 9 (Dropout) | (None, 1024) | 0 | Encoder[6][0] |
| dropout 10 (Dropout) | (None, 1024) | 0 | Encoder[7][0] |
| dropout 11 (Dropout) | (None, 1024) | 0 | Encoder[8][0] |
| dropout 12 (Dropout) | (None, 1024) | 0 | Encoder[9][0] |
| dropout 13 (Dropout) | (None, 1024) | 0 | Encoder[10][0] |
| dropout 14 (Dropout) | (None, 1024) | 0 | Encoder[11][0] |
| dropout 15 (Dropout) | (None, 1024) | 0 | Encoder[12][0] |
| dropout 16 (Dropout) | (None, 1024) | 0 | Encoder[13][0] |
| dropout 17 (Dropout) | (None, 1024) | 0 | Encoder[14][0] |
| dropout 18 (Dropout) | (None, 2048) | 0 | concatenate 1[0][0] |
| gaussian noise 3 (GaussianNoise | (None, 2048) | 0 | concatenate 1[0][0] |
| dropout 19 (Dropout) | (None, 2048) | 0 | concatenate 1[0][0] |
| gaussian noise 4 (GaussianNoise | (None, 2048) | 0 | concatenate 1[0][0] |

TABLE 9-continued

Model: "HEARTio"

| Layer (type) | Output Shape | Param # | Connected to |
|---|---|---|---|
| dropout 20 (Dropout) | (None, 2048) | 0 | concatenate 1[0][0] |
| label maker (Activation) | (None, 4) | 0 | dense 9[0][0] |
| pre-block (Activation) | (None, 4) | 0 | dense 3[0][0] |
| dense 4 (Dense) | (None, 5) | 10245 | dropout 1[0][0] |
| dense 5 (Dense) | (None, 17) | 34833 | dropout 2[0][0] |
| dense 6 (Dense) | (None, 17) | 34833 | dropout 3[0][0] |
| dense 7 (Dense) | (None, 20) | 40980 | gaussian noise 2[0][0] |
| dense 8 (Dense) | (None, 5) | 10245 | dropout 4[0][0] |
| dense 10 (Dense) | (None, 4) | 4100 | dropout 6[0][0] |
| dense 11 (Dense) | (None, 4) | 4100 | dropout 7[0][0] |
| dense 12 (Dense) | (None, 4) | 4100 | dropout 8[0][0] |
| dense 13 (Dense) | (None, 4) | 4100 | dropout 9[0][0] |
| dense 14 (Dense) | (None, 4) | 4100 | dropout 10[0][0] |
| dense 15 (Dense) | (None, 4) | 4100 | dropout 11[0][0] |
| dense 16 (Dense) | (None, 4) | 4100 | dropout 12[0][0] |
| dense 17 (Dense) | (None, 4) | 4100 | dropout 13[0][0] |
| dense 18 (Dense) | (None, 4) | 4100 | dropout 14[0][0] |
| dense 19 (Dense) | (None, 4) | 4100 | dropout 15[0][0] |
| dense 20 (Dense) | (None, 4) | 4100 | dropout 16[0][0] |
| dense 21 (Dense) | (None, 4) | 4100 | dropout 17[0][0] |
| dense 22 (Dense) | (None, 4) | 8196 | dropout 18[0][0] |
| dense 23 (Dense) | (None, 4) | 8196 | gaussian noise 3[0][0] |
| dense 24 (Dense) | (None, 4) | 8196 | dropout 19 [0][0] |
| dense 25 (Dense) | (None, 1) | 2049 | gaussian noise 4[0][0] |
| dense 26 (Dense) | (None, 1) | 2049 | dropout 20 [0][0] |
| block maker (Lambda) | (None, 4) | 0 | label maker[0][0] pre-block[0][0] |
| MI maker (Activation) | (None, 5) | 0 | dense 4[0][0] |
| beat maker (Activation) | (None, 17) | 0 | dense 5[0][0] |
| rhythm maker (Activation) | (None, 17) | 0 | dense 6[0][0] |
| SPECT maker (Activation) | (None, 20) | 0 | dense 7[0][0] |
| pred maker (Activation) | (None, 5) | 0 | dense 8[0][0] |
| lead 0 (Activation) | (None, 4) | 0 | dense 10[0][0] |
| lead 1 (Activation) | (None, 4) | 0 | dense 11[0][0] |
| lead 2 (Activation) | (None, 4) | 0 | dense 12[0][0] |
| lead 3 (Activation) | (None, 4) | 0 | dense 13[0][0] |
| lead 4 (Activation) | (None, 4) | 0 | dense 14[0][0] |
| lead 5 (Activation) | (None, 4) | 0 | dense 15[0][0] |
| lead 6 (Activation) | (None, 4) | 0 | dense 16[0][0] |
| lead 7 (Activation) | (None, 4) | 0 | dense 17[0][0] |
| lead 8 (Activation) | (None, 4) | 0 | dense 18[0][0] |
| lead 9 (Activation) | (None, 4) | 0 | dense 19[0][0] |
| lead 10 (Activation) | (None, 4) | 0 | dense 20[0][0] |
| lead 11 (Activation) | (None, 4) | 0 | dense 21[0][0] |
| bi block maker (Activation) | (None, 4) | 0 | dense 22[0][0] |
| BT maker (Activation) | (None, 4) | 0 | dense 23[0][0] |
| complication maker (Activation) | (None, 4) | 0 | dense 24[0][0] |
| EF maker (Activation) | (None, 1) | 0 | dense 25[0][0] |
| dis maker (Activation) | (None, 1) | 0 | dense 26[0][0] |

Total params: 32,605,288
Trainable params: 5,744,902
Non-trainable params: 26,860,38

What is claimed is:

1. A diagnostic tool, wherein the diagnostic tool comprises:
 a sensor for capturing N biosignals produced by a patient's heart, where N is greater than or equal to 1; and
 a computer device that implements a deep neural network that is trained iteratively through machine learning to generate multiple predictions about a heart condition of the patient, such that the deep neural network comprises multiple outputs, with each output corresponding to one of the multiple predictions about the heart condition of the patient, and wherein, after the deep neural network is trained to predict the multiple predictions, the computer device is configured to:
 convert, with an autoencoder, the N biosignals to a multi-dimensional input matrix for the deep neural network generated from the N biosignals captured by the sensor, wherein each of the N biosignals comprises a time component that is at least "T" seconds in duration, wherein T is at least one second; and
 process the multi-dimensional input matrix through the deep neural network, wherein the multiple outputs of the deep neural network from processing the multi-dimensional input matrix through the deep neural network correspond to the predictions about the heart condition of the patient, and wherein the multiple predictions comprise at least one prediction of coronary artery disease (CAD) of the patient,
 wherein:
 the deep neural network comprises a dense neural network (DenseNet) comprising a plurality of layers, wherein each layer after an input layer receives inputs from all preceding layers in the DenseNet;

the multi-dimensional matrix is input to the DenseNet;
the DenseNet produces a feature vector from the multi-dimensional matrix;
the deep neural network further comprises a classifier whose outputs are the multiple predictions about the heart condition of the patient; and
the input to the classifier comprises a concatenation of the feature vector from the DenseNet and a latent space representation from the autoencoder.

2. The diagnostic tool of claim 1, wherein the biosignal is an electrocardiogram (ECG) signal, and wherein N is 12.

3. The diagnostic tool of claim 1, wherein the biosignal is an electrocardiogram (ECG) signal, wherein N is less than 12, and wherein the computer device further implements the autoencoder trained via machine learning to generate 12-N biosignals based, at least in part, on a reconstruction loss function.

4. The diagnostic tool of claim 3, wherein the reconstruction loss function calculates a squared difference between a fast Fourier transform (FFT) between an input of the sensor and an output of the autoencoder.

5. The diagnostic tool of claim 3, wherein the autoencoder comprises:
an encoder configured to perform a lossy compression of the N biosignals captured by the sensor, wherein an output of the lossy compression is latent space representation; and
a decoder configured to receive the latent space from the encoder and convert the latent space representation into the multi-dimensional input matrix.

6. The diagnostic tool of claim 5, wherein the DenseNet is configured to generate the feature vector based, at least in part, on the multi-dimensional input matrix.

7. The diagnostic tool of claim 1, wherein the multiple outputs further comprise at least one of a beat classification and a rhythm classification.

8. The diagnostic tool of claim 1, wherein the multiple predictions further comprise at least one additional prediction selected from the group consisting of:
a Myocardial Infarction (MI), a risk of a Major Adverse Cardiovascular Event (MACE), a left anterior descending (LAD) coronary artery fractional flow reserve (FFR), an atherosclerotic cardiovascular disease (ACVD), cardiac hypertrophy, ventricle morphology, an abnormal ST-T wave, a conduction disorder, and a "70%" disease threshold.

9. The diagnostic tool of claim 1, wherein the at least one biosignal is an electroencephalogram (EEG).

10. The diagnostic tool of claim 1, wherein the sensor is a wearable device.

11. The diagnostic tool of claim 1, wherein T is greater than or equal to 5 second and less than or equal to 15 seconds.

12. The diagnostic tool of claim 1, further comprising a display coupled to the computer device, wherein the display is configured to visually represent the output of the deep neural network and the at least one prediction about CAD of the patient.

13. The diagnostic tool of claim 1, wherein the autoencoder comprises:
an encoder that generates, from the N biosignals, the latent space representation; and
a decoder that generates the multi-dimensional matrix from the latent space representation.

14. A method comprising:
training, with a computer system, iteratively through machine learning, a deep neural network to make multiple predictions about a heart condition of a patient, such that the deep neural network comprises multiple outputs, with each output corresponding to one of the multiple predictions about the heart condition of the patient; and
after training the deep neural network to predict the multiple predictions:
capturing, with a sensor, N biosignals produced by a patient's heart, where N is greater than or equal to 1;
converting, by an autoencoder of the computer system, the N biosignals to an input matrix for the deep neural network, wherein the input matrix comprises a multi-dimensional input matrix generated from the N biosignals that each comprises a time component that is at least "T" seconds in duration, where T is at least one second; and
processing, by the computer system, the multi-dimensional input matrix through the deep neural network, wherein the multiple outputs of the deep neural network from processing the multi-dimensional input matrix through the deep neural network correspond to the predictions about the heart condition of the patient, and wherein the multiple predictions comprise at least one prediction of coronary artery disease (CAD) of the patient,
wherein:
the deep neural network comprises a dense neural network (DenseNet) comprising a plurality of layers, wherein each layer after an input layer receives inputs from all preceding layers in the DenseNet;
the multi-dimensional matrix is input to the DenseNet;
the DenseNet produces a feature vector from the multi-dimensional matrix;
the deep neural network further comprises a classifier whose outputs are the multiple predictions about the heart condition of the patient; and
the input to the classifier comprises a concatenation of the feature vector from the DenseNet and a latent space representation from the autoencoder.

15. The method of claim 14, further comprising, by the computer system, randomly removing at least one of the N biosignals from the multi-dimensional input matrix prior to processing the multi-dimensional input matrix through the deep neural network.

16. The method of claim 14, further comprising, by the computer system, altering either the N biosignals captured by the sensor or a sensor configuration prior to processing the multi-dimensional input matrix through the deep neural network.

17. The method of claim 14, wherein the processing is iterative, wherein the deep neural network comprises a loss function, the method further comprises, by the computer system:
assessing, via the loss function, a weight loss associated with each of the N biosignals in the multi-dimensional input matrix based, at least in part, on a change in performance and/or a loss magnitude; and
changing the weight associated with each of the N biosignals for subsequent iterations based, at least in part, on the assessment of the loss function.

18. The method of claim 17, wherein the loss function is selected from a group consisting of a weighted binary cross entropy, a weighted categorical cross entropy, a weighted log cosh, and a binned mean log squared error.

19. The method of claim 17, wherein the loss function is semi-supervised and is either a multi-task learning loss (MTL) configured to correlate the latent space representation and each of a plurality of outputs or a semi-supervised information loss (SSIL) configured to find an equilibrium between information provided by each of the output and a plurality of possible outputs.

20. The method of claim 19, further comprising organizing, by the computer system, the sensor into one of a plurality of folders, wherein each of the plurality of folders is associated with at least one of the plurality of possible outputs.

21. The method of claim 19, further comprising:
assigning, by the computer system, a corresponding label to each of the plurality of outputs;
determining, by the computer system, that at least one output of the plurality of outputs does not have a corresponding label; and
creating, by the computer system, a label corresponding to the at least one output of the plurality of outputs.

22. A computer system comprising one or more processor cores, wherein the one or more processor cores are configured to:
train, iteratively through machine learning, a deep neural network to make multiple predictions about a heart condition of a patient, such that the deep neural network comprises multiple outputs, with each output corresponding to one of the multiple predictions about the heart condition of the patient; and
after training the deep neural network to predict the multiple predictions:
receive, from a sensor, N electrocardiogram (ECG) signals produced by a patient's heart and captured by the sensor;
convert, by an autoencoder, the N ECG signals to an input matrix for the deep neural network, wherein the input matrix comprises a multi-dimensional matrix generated from the N ECG signals that comprise a time component that is at least T seconds in duration, where T is at least one second; and
process the input matrix through the deep neural network, wherein the multiple outputs of the deep neural network from processing the input matrix through the deep neural network correspond to the predictions about the heart condition of the patient, and wherein the multiple predictions comprise at least one prediction of coronary artery disease (CAD) of the patient wherein:

the deep neural network comprises a dense neural network (DenseNet) comprising a plurality of layers, wherein each layer after an input layer receives inputs from all preceding layers in the DenseNet;

the multi-dimensional matrix is input to the DenseNet;

the DenseNet produces a feature vector from the multi-dimensional matrix;

the deep neural network further comprises a classifier whose outputs are the multiple predictions about the heart condition of the patient; and the input to the classifier comprises a concatenation of the feature vector from the DenseNet and a latent space representation from the autoencoder.

* * * * *